United States Patent
Schoepgens et al.

(10) Patent No.: US 11,077,040 B2
(45) Date of Patent: Aug. 3, 2021

(54) EMULSIONS FOR ENHANCED REDUCTIVE DECOLORATION OF KERATIN FIBERS

(71) Applicant: Henkel AG & Co. KGaA, Duesseldorf (DE)

(72) Inventors: Juergen Schoepgens, Schwalmtal (DE); Burkhard Mueller, Duesseldorf (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 747 days.

(21) Appl. No.: 15/570,845

(22) PCT Filed: Apr. 26, 2016

(86) PCT No.: PCT/EP2016/059227
§ 371 (c)(1),
(2) Date: Oct. 31, 2017

(87) PCT Pub. No.: WO2016/198203
PCT Pub. Date: Dec. 15, 2016

(65) Prior Publication Data
US 2018/0147128 A1     May 31, 2018

(30) Foreign Application Priority Data
Jun. 12, 2015   (DE) .......................... 102015210751.5

(51) Int. Cl.
| | | |
|---|---|---|
| *A61Q 5/08* | (2006.01) | |
| *A61K 8/46* | (2006.01) | |
| *A61K 8/34* | (2006.01) | |
| *A61Q 5/10* | (2006.01) | |
| *A45D 19/00* | (2006.01) | |
| *A45D 7/00* | (2006.01) | |

(52) U.S. Cl.
CPC ................ *A61K 8/46* (2013.01); *A61K 8/345* (2013.01); *A61Q 5/08* (2013.01); *A61Q 5/10* (2013.01); *A45D 19/0066* (2021.01); *A45D 2007/001* (2013.01); *A61K 2800/4324* (2013.01); *A61K 2800/884* (2013.01)

(58) Field of Classification Search
None
See application file for complete search history.

(56) References Cited

U.S. PATENT DOCUMENTS

| | | | |
|---|---|---|---|
| 6,171,347 B1 * | 1/2001 | Kunz ................. | C11D 3/38654 132/208 |
| 6,730,132 B1 | 5/2004 | Beckmann et al. | |
| 2010/0146710 A1 * | 6/2010 | Emmerling ............ | A61K 8/447 8/107 |

FOREIGN PATENT DOCUMENTS

| | | |
|---|---|---|
| DE | 102006053343.7 A1 | 8/2007 |
| DE | 102006022274.1 A1 | 11/2007 |
| DE | 102006053402.6 A1 | 5/2008 |
| EP | 1300136 A2 | 4/2003 |
| WO | 2007107310 A2 | 9/2007 |
| WO | 2007107312 A2 | 9/2007 |
| WO | 2008055756 A1 | 5/2008 |

OTHER PUBLICATIONS

EPO, International Search Report and Written Opinion issued in International Application No. PCT/EP2016/059227, dated Jul. 13, 2016.
Cyclanon ECO, Jan. 2000, BASF.

* cited by examiner

Primary Examiner — Jyothsna A Venkat
(74) Attorney, Agent, or Firm — Lorenz & Kopf, LLP

(57) ABSTRACT

The present disclosure relates to cosmetic agents for the reductive decoloration of colored keratinous fibers, more particularly human hair, containing a sulphinic acid derivative and at least one alcohol with from about 10 to about 30 carbon atoms. This combination is able to reduce the unpleasant odor during the decoloration process. The present disclosure also relates to a corresponding kit-of-parts, the use of cosmetic agents and the kit-of-parts, as well as to an application method using the cosmetic agents and the packaging unit.

2 Claims, No Drawings

EMULSIONS FOR ENHANCED REDUCTIVE DECOLORATION OF KERATIN FIBERS

CROSS-REFERENCE TO RELATED APPLICATION

This application is a U.S. National-Stage entry under 35 U.S.C. § 371 based on International Application No. PCT/EP2016/059227, filed Apr. 26, 2016 which was published under PCT Article 21(2) and which claims priority to German Application No. 10 2015 210 751.2, filed Jun. 12, 2015, which are all hereby incorporated in their entirety by reference.

TECHNICAL FIELD

The present disclosure relates to cosmetic agents for the reductive decoloration of colored keratinous fibers containing at least one sulphinic acid derivative and at least one alcohol with from about 10 to about 30 carbon atoms. The present disclosure also relates to a kit-of-parts, a method for the reductive decoloration of colored keratinous fibers, as well as use of the cosmetic agents as contemplated herein and kit-of-parts as contemplated herein for reductive decoloration, as well as for reducing the unpleasant odor produced by the reductive decoloration of colored keratinous fibers.

BACKGROUND

Changing the style and color of the hair constitutes an important area of modern cosmetics. The hair's appearance can be adapted both to current fashion trends and also to the particular preferences of each and every consumer. Coloring hair in a stylish manner or laminating graying or white hair with modern or natural color shades is normally achieved by employing color-changing agents. In addition to a strong color effect, these agents have additional features, such as increasing the hair volume.

Various coloring systems are known from the prior art for preparing color-changing cosmetic agents, more particularly for skin or for keratin fibers such as human hair, for example.

To achieve permanent, intense colors with corresponding fastness properties, so-called oxidative dyes are used. Said dyes usually contain oxidative dye precursors, so-called developer components and coupler components. The developer components join together or couple with one or more coupler components to form, under the influence of oxidants or atmospheric oxygen, the actual colorants per se. Indeed, the oxidative dyes are exemplified by outstanding, long-lasting color results. To achieve natural-looking colors, however, a mix from a large number of oxidative dye intermediates must normally be used; in many cases, partially-oxidizing dyes are still used to create the tinting effect.

For temporary colors, dyes or tints containing so-called partially-oxidizing agents are normally used as the coloring component. These are dye molecules that coat the substrate itself and do not require an oxidative process to create the color. These dyes include Henna, which has been known to color skin and hair since ancient times. Said dyes are usually much more sensitive to shampooing than oxidative dyes, and therefore a highly undesirable shade shift or a visible homogeneous color loss occurs at a much earlier time.

Moreover, it is possible to color hair using precursor stages of the natural hair dye melanin. Once said precursor stages have been applied, nature-like dyes form in the hair during the course of the oxidative processes. In said method, 5,6-dihydroxyindoline is used as the dye precursor. Particularly if agents containing 5,6-dihydroxyindoline are repeatedly applied, the natural hair color of people with graying hair can be restored. The color effect can be achieved by employing atmospheric oxygen as the only oxidant, thereby eliminating the need for further oxidants. In the case of people whose hair was originally medium-blond to brown, 5,6-dihydroxyindoline can be used as the only precursor. For application on people whose hair was originally red and more particularly dark to black, on the other hand, satisfactory results can often be achieved only if other dye components, more particularly special oxidative dye precursors, are also used.

With the aforementioned dyeing methods, however, the achieved coloration, more particularly hair coloration, may sometimes need to be reversed, either whole or in part, for various reasons. This might be requested by the consumer if, for example, the fibers appear to be darker after coloring or the desired shade has not been achieved. A decoloration of dyed fibers may also be required if the fibers, more particularly hair, are to be colored or tinted to a certain shade only for a specific occasion, and the original hair color is to be restored after a few days.

Agents and methods for the decoloration of colored fibers, more particularly hair, are known from the prior art. For example, a decoloration of colored hair can be achieved by oxidatively post-treating colored hair with an ordinary blonding agent. However, said method causes damage to the hair due to the use of a strong oxidant.

Moreover, reductive processes for the decoloration of colored fibers, more particularly hair, are also known. The reductive decoloration is achieved by reducing the dyes present on the keratinous fibers and/or hair. This method involves reducing the double bonds present in the dyes, thus interrupting the chromophoric system of the dyes and converting the dye into a colorless form, also referred to as reduced leuco form.

European Patent Application EP 1 300 136 A2 discloses, for example a process for hair treatment, wherein the hair is first colored and then reductively decolored. In this process, the reductive decoloration is achieved by using a dithionite salt in combination with a tenside. WO 2008/055756 A2 describes the reductive decoloration of keratinous fibers using a mixture from a reducing agent and an absorption agent.

A general problem with the reductive decoloration agents known from the prior art is that although the dyed keratinous fibers can be decolored by employing the reducing agent, said decoloration is not long-lasting. Particularly in the case of oxidatively colored hair, where the coloration is produced by oxidative dye precursors of the developer and coupler type, colors with very good fastness properties can be attained in some cases. If reductive decoloration agents are used, said dyes are indeed reductively transferred to uncolored compounds, but said uncolored compounds remain in the hair even after the reductive decoloration process due to the good fastness properties. Under the influence of atmospheric oxygen, said uncolored compounds can be re-oxidized, thereby bringing about re-coloration. As a rule, such re-coloration does not correspond to the shade of the coloration prior to the decoloration. Instead, it can appear extremely unattractive and is therefore undesirable for the user of the reductive decoloration agent. Moreover, the odor produced by said decoloration agent is extremely unpleasant and as such perceived by the consumer to be unpleasant.

BRIEF SUMMARY

Cosmetic agents, kits-of-parts, and methods for coloration and reductive coloration of keratinous fibers are provided herein. In an embodiment, a cosmetic agent for the reductive decoloration of dyed keratinous fibers is proved. The cosmetic agent includes, in a cosmetic carrier, at least compound of I of the Formula (I)

$$A[(CR^1R^2)SO_2M]_{p,q} \quad (I)$$

wherein

A denotes $N(R^3)_{3-q}$ or $O(R^4)_{2-p}$ $R^1$, $R^2$, $R^4$ denote independently a hydrogen atom or a $C_1$-$C_6$-alkyl group, $R^3$ denotes identical or various radicals selected from a hydrogen atom, a $C_1$-$C_{20}$ alkyl group, a $C_3$-$C_8$ cycloalkyl group, optionally substituted by one to three $C_1$-$C_4$ alkyl radicals, M denotes identical or various residues selected from a hydrogen atom or an equivalent of an alkali, alkali earth or metal ions, p denotes the integer 1 or 2, q denotes the integer 2 or 3, wherein at least one of the radicals $R^{1,}$ $R^2$, $R^4$ denotes a $C_1$-$C_6$ alkyl group, when A denotes $O(R^4_{2-p})$, and $R^3$ does not denote a hydrogen atom when q is equal to 1. The cosmetic agent further includes at least one alcohol with from 10 to 30 hydrogen atoms in a total quantity of from about 0.1 to about 20 wt. %, relative to the total weight of the cosmetic agent.

In another embodiment, a kit-of-parts is provided for the reductive decoloration of dyed keratinous fibers. The kit of parts includes at least two preparations (1) and (2) packaged separately from one another. The first preparation (1) includes, in a cosmetic carrier, at least one compound I of the Formula (I), and optionally at least one compound II of the Formula (II). Formula (I) is $$A[(CR^1R^2)SO_2M]_{p,q} \quad (I)$$

wherein

A denotes $N(R^3)_{3-q}$ or $O(R^4)_{2-p}$ $R^1$, $R^2$, $R^4$ denote independently a hydrogen atom or a $C_1$-$C_6$-alkyl group, $R^3$ denotes identical or various radicals selected from a hydrogen atom, a $C_1$-$C_{20}$ alkyl group, a $C_3$-$C_8$ cycloalkyl group, optionally substituted by one to three $C_1$-$C_4$ alkyl radicals M denotes identical or various residues selected from a hydrogen atom or an equivalent of an alkali, alkali earth or metal ions, p denotes the integer 1 or 2, q denotes the integer 2 or 3, wherein at least one of the radicals $R^1$, $R^2$, $R^4$ denotes a $C_1$-$C_6$ alkyl group, when A denotes $O(R^4_{2-p})$, and $R^3$ does not denote a hydrogen atom when q is equal to 1, and at least one alcohol with from 10 to 30 hydrogen atoms in a total quantity of from about 0.1 to about 20 wt. %, relative to the total weight of the cosmetic agent. Formula (II) is $$A[(CR^1R^2)SO_3M]_{p,q} \quad (II)$$

wherein

A denotes $N(R^3)_{3-q}$ or $O(R^4)_{2-p}$ $R^1$, $R^2$, $R^4$ denote independently a hydrogen atom or a $C_1$-$C_6$-alkyl group, $R^3$ denotes identical or various radicals selected from a hydrogen atom, a $C_1$-$C_{20}$ alkyl group, a $C_3$-$C_8$ cycloalkyl group, optionally substituted by one to three $C_1$-$C_4$ alkyl radicals M denotes identical or various residues selected from a hydrogen atom or an equivalent of an alkali, alkali earth or metal ions, p denotes the integer 1 or 2, q denotes the integer 2 or 3, wherein at least one of the radicals $R^1$, $R^2$, $R^4$ denotes a $C_1$-$C_6$ alkyl group, when A denotes $O(R^4_{2-p})$, and $R^3$ does not denote a hydrogen atom if q is equal to 1. The second preparation (2) includes at least one inorganic and/or organic acid. Preparation (1) and/or preparation (2) include at least one alcohol with from 10 to 30 carbon atoms in a total quantity of from about 0.1 to about 20 wt. %, relative to the total weight of preparation (2).

In another embodiment, a method for coloration and reductive coloration of keratinous fibers is provided. The method includes the following method steps in the stated sequence:

(a) Application of a cosmetic colorant including at least one partially oxidizing dye and/or at least one oxidative dye precursor to keratinous fibers (b) Allowing the colorant to take effect for a period of from about 5 to about 60 minutes (c) Rinsing out the colorant (d) Application of a decoloration agent onto keratinous fibers (e) Allowing the colorant to take effect at a temperature of from about 20 to about 45° C for a period of from about 5 to about 60 minutes, (f) Rinsing out the decoloration agent, and (g) optionally, application of a post-treatment agent to the keratinous fibers, wherein said post-treatment agent comprises at least one tenside selected from the group of anionic tensides, cationic tensides, non-ionic tensides, amphoteric and/or zwitterionic tensides, as well as the mixtures thereof. The decoloration agent includes at least compound of I of the Formula (I)

$$A[(CR^1R^2)SO_2M]_{p,q} \quad (I)$$

wherein

A denotes $N(R^3)_{3-q}$ or $O(R^4)_{2-p}$ $R^1$, $R^2$, $R^4$ denote independently a hydrogen atom or a $C_1$-$C_6$-alkyl group, R3 denotes identical or various radicals selected from a hydrogen atom, a $C_1$-$C_{20}$ alkyl group, a $C_3$-$C_8$ cycloalkyl group, optionally substituted by one to three $C_1$-$C_4$ alkyl radicals M denotes identical or various residues selected from a hydrogen atom or an equivalent of an alkali, alkali earth or metal ions, p denotes the integer 1 or 2, q denotes the integer 2 or 3, wherein at least one of the radicals $R^1$, $R^2$, $R^4$ denotes a $C_1$-$C_6$ alkyl group, when A denotes $O(R^4_{2-p})$, and $R^3$ does not denote a hydrogen atom when q is equal to 1. The decoloration agent further includes at least one alcohol with from 10 to 30 hydrogen atoms in a total quantity of from about 0.1 to about 20 wt. %, relative to the total weight of the cosmetic agent.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The present disclosure addresses the problem of preparing a cosmetic agent for the reductive decoloration of dyed keratinous fibers, which result in a largely complete and long-lasting decoloration of the dyed fibers. Particularly on fibers colored beforehand with oxidative dyes based on oxidative dye precursors of the developer and coupler types, the cosmetic agent is said to have a good decoloration effect. Moreover, there is said to be no re-coloration, shade shifts and/or post-darkening after decoloration under the effect of atmospheric oxygen. In addition, the unpleasant odor occurring when said agents are used is said to be minimized. Finally, the cosmetic agent is supposed to be toxicologically safe and can be used under cosmetically safe conditions.

It has now unexpectedly emerged that the use of certain sulphinic acids in combination with special alcohols leads to very good decoloration effects on oxidatively colored fibers, and that no re-coloration, shade shifts or post-darkening occurs. An especially good decoloration effect without re-coloration or post-darkening is achieved on fibers colored beforehand with oxidative dyes. Moreover, the use of the aforementioned combination leads to an minimized unpleasant odor during use. The compounds used in the cosmetic agents as contemplated herein are toxicologically safe and can be used in conditions that do not cause excess damage to the hair or scalp.

A first subject matter of the present disclosure is therefore a cosmetic agent for the reductive decoloration of dyed keratinous fibers, more particularly human hair, containing in a cosmetic carrier.
a) at least compound of I of the Formula (I)

wherein
A denotes $N(R^3)_{3-q}$ or $O(R^4)_{2-p}$
$R^1$, $R^2$, $R^4$ denote independently a hydrogen atom or a $C_1$-$C_6$-alkyl group,
$R^3$ denotes identical or various radicals selected from a hydrogen atom, a $C_1$-$C_{20}$ alkyl group, a $C_3$-$C_8$ cycloalkyl group, substituted by one to three $C_1$-$C_4$ alkyl radicals if necessary
M denotes identical or various residues selected from a hydrogen atom or an
equivalent of an alkali, alkali earth or metal ions, more particularly for sodium, potassium, ½ magnesium, ½ calcium, ½ zinc, or an ammonium ion ($NH_4^+$),
p denotes the integer 1 or 2,
Q denotes the integer 1, 2 or 3,
wherein
at least one of the radicals $R^1$, $R^2$, $R^4$ denotes a $C_1$-$C_6$ alkyl group, if A denotes $O(R^4_{2-p})$, and
$R^3$ does not denote a hydrogen atom if q is equal to 1, and
b) at least one alcohol with from 10 to about 30 hydrogen atoms in a total quantity of from about 0.1 to about 20 wt. %, relative to the total weight of the cosmetic agent.

Method for the reductive post-treatment of polyester textiles with sulphinic acid derivatives of the Formula (I) are known from EP 0 914 516 B1, for example. During the post treatment of polyester textiles, the sulphinic acid derivatives of the Formula (I), however, are used solely under conditions at temperatures of from about 50 to about 100° C., said conditions being less acceptable from a cosmetic perspective. It has now unexpectedly emerged that said sulphinic acid derivatives are also suitable for decoloring keratinous fibers and/or human hair, if the keratinous fibers were colored beforehand with partially oxidative dyes and/or oxidative dye precursors (developers and couplers). Particularly surprising in this context was the fact that the reductive decoloration of keratinous fibers occurs even at physiologically-acceptable conditions, i.e. Temperatures of below about 45° C.

Substituents $R^1$ to is $R^4$ of the Compound I of the Formula (I) are explained below by way of example: Examples of a $C_1$-$C_6$ alkyl group are the groups methyl, ethyl, propyl, isopropyl, n-butyl, s-butyl and t-butyl, n-pentyl and n-hexyl. Examples of $C_7$-$C_{20}$ alkyl groups are the groups in n-octyl, n-decyl, n-dodecyl, n-tetradecyl, n-hexadecyl and n-octadecyl. Examples of a $C_3$-$C_6$ cycloalkyl group are the cyclopropyl groups cyclopentyl groups or cyclohexyl groups.

As contemplated herein, the expressions "keratinous fibers and keratin fibers" suggest fur, wool, feathers as well as human hair. According to the present disclosure, a cosmetic means for coloring human hair is most preferred.

As contemplated herein, the expression "dyed keratinous fibers" also suggest keratinous fibers, which have been dyed by employing cosmetic dyes known to a person skilled in the art. The expression "dyed keratinous fibers" means in particular fibers that have been dyed by employing oxidative dyes (developers and couplers) known from the prior art. In this context, explicit reference is made to the known monographies, e.g. Kh. Schrader, Grundlagen und Rezepturen der Kosmetika [Cosmetic principles and formulas, 2nd Edition, Hüthig Buch Verlag, Heidelberg, 1989, which reflect the corresponding knowledge of a person skilled in the art.

In addition, the expression "fatty alcohols" according to the present disclosure means aliphatic, long-chained, monovalent, primary alcohols, which have unbranched hydrocarbon radicals containing from 6 to about 30 carbon atoms. The hydrocarbon radicals can be either saturated or mono- or polyunsaturated.

Finally, the expression "fatty acids" according to the present disclosure means aliphatic monocarboxylic acids with unbranched carbon radicals, which have hydrocarbon radicals containing from 6 to about 30 carbon atoms. The hydrocarbon radicals can be either saturated or mono- or polyunsaturated.

Unless otherwise specified, the total quantity with respect to the components of the cosmetic agent as contemplated herein refers to the total quantity of active substance for the respective component. Moreover, the indication of the total quantity with respect to the components of the cosmetic agent refers—unless otherwise specified—to the total weight of the ready-to-use decoloration agent, i.e. the agent which is ready to use and can be applied directly by the user to the previously dyed keratinous fibers.

The cosmetic agents as contemplated herein are dyes which are used to decolor previously dyed keratinous fibers, more particularly human hair. The dyed keratinous fibers are usually fibers which have been colored beforehand by employing conventional oxidative dyes and/or partially oxidative dyes known to a person skilled in the art.

The decloration agents are suitable for removing colors produced on the keratinous fibers by employing oxidizing dyes based on developer and coupler components. If the following compounds were used as developers, the colors thus produced can easily be removed effectively and almost without subsequent post-darkening by employing the decoloration agent: p-phenylendiamine, p-toluylendiamine, N,N-bis-((3-hydroxyethyl)-p-phenylendiamine, 4-N,N-bis-((3-hydroxyethyl)-amino-2-methylaniline, 2-((3-hydroxyethyl)-p-phenylendiamine, 2-(α,β-dihydroxyethyl)-p-phenylendiamine, 2-hydroxymethyl-p-phenylendiamine, bis-(2-hydroxy-5-aminophenyl)-methane, p-aminophenol, 4-amino-3-methylphenol, 2,4,5,6-tetraaminopyrimidine, 4-hydroxy-2,5,6-triaminopyrimidine, 2-hydroxy-4,5,6-triaminopyrimidine and/oder 4,5-diamino-1-((3-hydroxyethyl)-pyrazol.

If the following compounds were used as couplers, the colors produced thereby can likewise be removed with very good decoloration results: m-phenylendiamine derivates, naphthols, resorcin and resorcin derivates, pyrazolone and m-aminophenol derivatives. Particularly suitable coupler substances are 1-naphthol, 1,5-, 2,7- and 1,7-dihydroxy naphthaline, 5-amino-2-methylphenol, m-aminophenol, resorcine, resorcine monomethylether, m-phenylendiamine, 1-phenyl-3-methyl-pyrazolone-5,2,4-dichlor-3-aminophenol, 1,3-bis-(2',4'-diaminophenoxy)-propane, 2-chlor-resorcine, 4-chlor-resorcine, 2-chlor-6-methyl-3-aminophenol, 2-amino-3-hydroxypyridine, 2-methylresorcine, 5-methylresorcine and 2-methyl-4-chlor-5-aminophenol, 1-naphthol, 1,5-dihydroxy naphthaline, 2,7-dihydroxynaphthaline, 1,7-dihydroxynaphthaline, 3-aminophenol, 5-amino-2-methylphenol, 2-amino-3-hydroxypyridine, resorcine, 4-chlorresorcine, 2-chlor-6-methyl-3-aminophenol, 2-methylresorcine, 5-methylresorcine, 2,5-dimethylresorcine and 2,6-dihydroxy-3,4-dimethylpyridine.

The decoloration agents as contemplated herein are designed to remove said colors and therefore preferably contain no dyes, more particularly no oxidative dye precursors of the developer type and/or coupler type, as well as partially-oxidizing dyes.

Therefore, the total quantity of all the partially oxidizing dyes and/or oxidative dye precursors contained in the cosmetic agents preferably contain a maximum of about 0.2 wt. %, more preferably a maximum of about 0.1 wt. %, even more preferably a maximum of about 0.05 wt. %, and most preferably a maximum of about 0.01 wt. %, relative to the total weight of the cosmetic agent.

The cosmetic agents as contemplated herein contain a cosmetically tolerant carrier. As contemplated herein, the cosmetically tolerant carrier is hydrous, alcoholic or hydrous-alcoholic. According to the present disclosure, creams, emulsions, gels or tenside-containing, foaming solutions for example, such as shampoos, foam aerosols or other preparations suitable for application on the hair, can be used. Most preferably, the cosmetic agents exist in the form of emulsions, since surprisingly the use of such emulsions reduces the unpleasant odor produced during the reductive decoloration process.

As contemplated herein, a hydrous carrier contains at least about 30 wt. %, more particularly at least about 50 wt. %, of water relative to the total weight of the cosmetic agent.

According to the present disclosure, hydrous-alcoholic carriers mean aqueous compositions, containing a $C_1$-$C_4$ alcohol in a total quantity of from about 3 to about 90 wt. %, relative to the total weight of the cosmetic agent, more particularly ethanol and/or isopropanol.

The agent as contemplated herein can additionally contain other organic solvents, such as methoxybutanol, ethyldiglycol, 1,2-propylenglycol, n-propanol, n-butanol, n-butylenglycol, glycerine, diethylenglycolmonoethylether, and Diethylenglycolmono-n-butylether. All water-soluble organic solvents are preferred, wherein the solvent is contained in a total quantity of from about 0.1 to about 30 wt. %, preferably from about 1 to about 20 wt. %, more particularly from about 2 to about 10 wt. %, relative to the total weight of the cosmetic agent.

The cosmetic agent as contemplated herein contains as the first integral component a) a sulphinic acid derivative of the Formula (I).

Sulphinic acid derivatives of the Formula (can have, as Radical A, either a grouping $N(R^3)_{3-q}$ or a grouping $O(R^4)_{2-p}$. If A denotes the grouping $N(R^3)_{3-q}$ then the sulphinic acid derivatives have the formula $N(R^3)_{3-q}[(CR^1R^2)SO_2M]_q$.

If, on the other hand, A in the Formula denotes the grouping $O(R^4)_{2-p}$, then the compounds are sulphinic acid derivatives with formula $O(R^4)_{2-p}[(CR^1R^2)SO_2M]_p$, wherein p denotes the integer 1 or 2 and at least one of the radicals $R^1$, $R^2$, $R^4$ denotes a $C_1$-$C_6$ alkyl group. If, therefore, p denotes the integer 1, then the sulphinic acid derivative is a compound of the formula $O(R^4)_1[(CR^1R^2)SO_2M]_1$. If, on the other hand, p denotes the integer 2, then the sulphinic acid derivative has the formula $O[(CR^1R^2)SO_2M]_2$.

The best decoloration effects were achieved using a compound of the Formula (I), wherein Radical A denotes $N(R^3)_{3-q}$. It is therefore particularly preferable for the Formula (I) to denote the Radical A for $N(R^3)_{3-q}$. The cosmetic agent as contemplated herein therefore most preferably contains a sulphinic acid derivative of formula $N(R^3)_{3-q}[(CR^1R^2)SO_2M]_q$.

In this context, it is advantageous for q to denote in the Formula (I) the integers 2 or 3, preferably for the integer 3. The most preferably used sulphinic acid derivatives of the Formula (I) used according to this present disclosure are therefore the compounds of formulas $N(R^3)_1[(CR^1R^2)SO_2M]_2$ (p=2) and $N[(CR^1R^2)SO_2M]_3$ (p=3).

Radicals $R^1$ and $R^2$ in Formula (I) denote independently a hydrogen atom or a $C_1$-$C_6$ alkyl group. With respect to the decoloration effect of the cosmetic means as contemplated herein, it is preferable for Radicals $R^1$ and $R^2$ to denote independently in the Formula (I) a hydrogen atom or a methyl group, more preferably a hydrogen atom. It is therefore advantageous for sulphinic acid derivatives of formulas $N(R^3)_1[(CH_2)SO_2M]_2$, $N(R^3)_2[(CH_2)SO_2M]$ and $N[(CH_2)SO_2M]_3$ to be used in the cosmetic agents as contemplated herein.

In the Formula (I), M denotes identical or various residues selected from a hydrogen atom or an equivalent of an alkali, alkali earth or metal ions, more particularly for sodium, potassium, ½ magnesium, ½ calcium, ½ zinc, or an ammonium ion ($NH^4_+$).

The sulphinic acid derivatives of Formula (I) as contemplated herein are compounds, each of which—bound to a nitrogen atom or to an oxygen atom—contain a sulphinic acid methyl group substituted with Radicals $R^1$ and $R^2$, which is also referred to as methane sulphinic acid groups. In each of these structured units, the sulphinic methyl group can exist in protonated form, i.e. M stands for a hydrogen atom. The sulphinic methyl group can, however, also exist in the form of its salt, preferably in the form of its sodium salt, potassium salt or zinc salt.

In the cases where the sulphinic acid derivative of the Formula (I) as contemplated herein contains multiple sulphinic acid methyl groups, one of said groups can be protonated (i.e. M is equivalent to hydrogen), whereas a further (or the further) sulphinic methyl group(s) exist in the form of their salt (i.e. M is equivalent to an alkali, earth alkali, metal or ammonium ion). Moreover, the present disclosure includes mixtures of protonated sulphinic acids of the Formula (I) with deprotonated sulphinic acids of the Formula (I). This mixtures can occur when the sulphinic acid derivative(s) of the Formula (I) exist in a cosmetic carrier in a dissolved form and the protonated sulphinic acids are in equilibrium with the deprotonated sulphinic acids.

As contemplated herein, it is most preferable for M to denote in the Formula (I) M identical or different radicals, selected from a hydrogen atom or an equivalent of an alkali, earth alkali or metal ion from the group of sodium, potassium and ½ zinc.

With respect to the decoloration result, it is advantageous for the cosmetic agent as contemplated herein to contain highly specific sulphinic acids of the Formula (I). It is therefore preferable for the cosmetic agent to contain at least one compound I of the Formula (I), which is selected from the group of $HN(CH_2SO_2Na)_2$, disodium [(sulfinatomethyl)amino]methanesulfinate $HN(CH_2SO_2K)_2$, dipotassium [(sulfinatomethyl)amino]methanesulfinate $HN(CH_2SO_2H)_2$, [(sulfinomethyl)amino]methane sulphinic acid $N(CH_2SO_2Na)_3$, trisodium [bis(sulfinatomethyl)amino]methansulfinate $N(CH_2SO_2K)_3$, tripotassium [bis(sulfinatomethyl)amino] methansulfinate $N(CH_2SO_2H)_3$, [Bis(sulfinomethyl)amino]methane sulphinic acid $H_2NCH(CH_3)SO_2Na$, sodium 1-aminoethane-1-sulfinate $H_2NCH(CH_3)SO_2K$, potassium 1-aminoethane-1-sulfinate $H_2NCH(CH_3)SO_2H$, 1-aminoethane-1-sulphinic acid, $HN(CH(CH_3)SO_2Na)_2$, disodium 1-[(1-sulfinatoethyl)amino]ethane-1-sulfinate $HN(CH(CH_3)SO_2K)_2$, dipotassium 1-[(1-sulfinatoethyl)amino]ethane-1-sulfinate $HN(CH(CH_3)SO_2H)_2$, 1-[(1-sulfinoethyl)amino]ethane-1-sulphinic acid $N(CH(CH_3)SO_2Na)_3$, trisodium 1-[Bis(1-sulfinatoethyl)amino]ethane-1-sulfinate $N(CH(CH_3)SO_2K)_3$, tripotassium 1-[Bis(1-sulfinatoethyl)amino]ethane-1-sulinate $N(CH(CH_3)SO_2H)_3$, 1-[bis(1-sulfinoethyl)amino]ethane-1-sulphinic acid, as well as the compounds thereof.

The most preferred cosmetic agents according to the present disclosure are those containing at least one compound I of the Formula (Ia)

$$N(CH_2SO_2Na)_3 \quad (Ia).$$

Use of the aforementioned compounds of the Formula (Ia), which is also referred to as trisodium[bis(sulfinatomethyl)amino]methane sulfinate, in the cosmetic agents as contemplated herein creates an excellent decoloration effect, particularly on keratinous fibers dyed with oxidative dyes. Moreover, no re-coloration or post-darkening at all occurs after the decoloration process.

The sulphinic acid derivative(s) of the Formula (I) is/are preferably used within specific quantity ranges. As contemplated herein It is therefore advantageous for the at least one compound (I) of the Formula (I) to be contained in a total quantity of from about 0.1 to about 30.0 wt. %, preferably from about 0.2 to about 20.0 wt. %, more preferably from about 0.3 to about 10.0 wt. % and more preferably from about 0.5 to about 6.0 wt. %, relative to the total weight of the cosmetic means. Total quantity means the quantity of all compounds of the Formula (I) contained in the cosmetic agent as contemplated herein.

As a second integral component b) the cosmetic agent as contemplated herein contains at least one alcohol with from 10 to about 30 hydrogen atoms in a total quantity of from about 0.1 to about 20 wt. %, relative to the total weight of the cosmetic agent.

The most preferred alcohol b) has from about 10 to about 30 carbon atoms selected from the group of 1-decanol, lauryl alcohol, myristyl alcohol, cetyl alcohol, stearyl alcohol, arachylalcohol and behenyl alcohol, lignoceryl alcohol, ceryl alcohol, montanyl alcohol, as well as the mixtures thereof, more particularly from a mixture of cetyl alcohol and stearyl alcohol Use of the aforementioned alcohols in the cosmetic agents as contemplated herein leads to a reduced unpleasant odor during the reductive decoloration of dyed keratinous fibers by employing the cosmetic agents as contemplated herein.

According to the present disclosure, the at least one alcohol b) is used in a specific total quantity. Cosmetic agents preferred as contemplated herein therefore contain at least one alcohol b) in a total quantity of from about 0.5 to about 18 wt. %, preferably from about 1.0 to about 15 wt. %, more preferably from about 1.2 to about 12 wt. %, most preferably from about 1.5 to about 10 wt. %, relative to the total weight of the cosmetic agent.

In addition to the compounds of the Formula (I), a sulphonic acid of the Formula (II) can be used in the cosmetic agent as contemplated herein. The cosmetic agent therefore preferably contains in addition a compound II of the Formula (II)

$$A[(CR^1R^2)SO_3M]_{p,q} \quad (II)$$

wherein

A denotes $N(R^3)_{3-q}$ or $O(R^4)_{2-p}$ $R^1$, $R^2$, $R^4$ denote independently a hydrogen atom or a $C_1$-$C_6$-alkyl group, $R^3$ denotes identical or various radicals selected from a hydrogen atom, a $C_1$-$C_{20}$ alkyl group, a $C_3$-$C_8$ cycloalkyl group, substituted by one to three $C_1$-$C_4$ alkyl radicals if necessary M denotes identical or various residues selected from a hydrogen atom or an equivalent of an alkali, alkali earth or metal ions, more particularly for sodium, potassium, ½ magnesium, ½ calcium, ½ zinc, or an ammonium ion ($NH_4^+$), p denotes the integer 1 or 2, q denotes the integer 2 or 3, wherein at least one of the radicals $R^1$, $R^2$, $R^4$ denotes a $C_1$-$C_6$ alkyl group, if A denotes $O(R^4_{2-p})$, and $R^3$ does not denote a hydrogen atom if q is equal to 1.

With respect to Radicals A, $R^1$ to $R^4$ and M, as well as p and q of the Formula (II), reference is made to the aforementioned embodiments, which apply equally to this embodiment.

Sulphonic acid derivatives of the Formula (II) can have, as Radical A, either a grouping $N(R^3)_{3-q}$ or a grouping $O(R^4)_{2-p}$. If A denotes the grouping $N(R^3)_{3-q}$ then the sulphonic acid derivatives have the formula $N(R^3)_{3-q}[(CR^1R^2)SO_3M]_q$.

If, on the other hand, A in the Formula II denotes the grouping $O(R^4)_{2-p}$, then the compounds are sulphonic acid derivatives with formula $O(R^4)_{2-p}[(CR^1R^2)SO_3M]_p$, wherein p denotes the integer 1 or 2 and at least one of the radicals $R^1$, $R^2$, $R^4$ denotes a $C_1$-$C_6$ alkyl group. If, therefore, p denotes the integer 1, then the sulphinic acid derivative is a compound of the formula $O(R^4)_1[(CR^1R^2)SO_3M]_1$. If, on the other hand, p denotes the integer 2, then the sulphinic acid derivative has the formula $O[(CR^1R^2)SO_3M]_2$.

An improved decoloration effect was achieved with the additional use of a compound of the Formula (II), in which the Radical A denotes $N(R^3)_{3-q}$. It is therefore particularly preferable for the Formula (II) to denote the Radical A for $N(R^3)_{3-q}$. The cosmetic agent as contemplated herein therefore most preferably contains a sulphonic acid derivative of formula $N(R^3)_{3-q}$ $[(CR^1R^2)SO_3M]_q$.

In this context, it is advantageous for q to denote in the Formula (II) the integers 2 or 3, preferably for the integer 3. The most preferably used sulphonic acid derivatives of the Formula (II) used according to this present disclosure are therefore the compounds of formulas $N(R^3)_1$ $[(CR^1R^2)SO_3M]_2$ (p=2) and N $[(CR^1R^2)SO_3M]_3$ (p=3).

Radicals $R^1$ and $R^2$ in Formula (II) denote independently a hydrogen atom or a $C_1$-$C_6$ alkyl group. With respect to the decoloration effect of the cosmetic means as contemplated herein, it is preferable for Radicals $R^1$ and $R^2$ to denote independently in the Formula (II) a hydrogen atom or a methyl group, more preferably a hydrogen atom. It is therefore advantageous for sulphonic acid derivatives of formulas $N(R^3)_1[(CH_2)SO_3M]_2$ and $N[(CH_2)SO_3M]_3$ to be used in the cosmetic agents as contemplated herein.

In the Formula (II), M denotes identical or various residues selected from a hydrogen atom or an equivalent of an alkali, alkali earth or metal ions, more particularly for sodium, potassium, ½ magnesium, ½ calcium, ½ zinc, or an ammonium ion ($NH_4^+$).

The sulphonic acid derivatives of Formula (II) as contemplated herein are compounds, each of which—bound to a nitrogen atom or to an oxygen atom—contain a sulfomethyl group substituted with Radicals $R^1$ and $R^2$, which is also referred to as methane sulphonic acid groups. In each of these structured units, the sulfomethyl group can exist in protonated form, i.e. M stands for a hydrogen atom. The sulfomethyl group can, however, also exist in the form of its salt, preferably in the form of its sodium salt, potassium salt or zinc salt.

In the cases where the sulphnic acid derivative of the Formula (II) contains multiple sulphonic acid methyl groups, one of said groups can be protonated (i.e. M is equivalent to hydrogen), whereas a further (or the further) sulfomethyl group(s) exist in the form of their salt (i.e. M is equivalent to an alkali, earth alkali, metal or ammonium ion). Moreover, the present disclosure includes mixtures of protonated sulphonic acids of the Formula (II) with deprotonated sulphonic acids of the Formula (II). This mixtures can occur when the sulphonic acid derivative(s) of the Formula (II) exist in a cosmetic carrier in a dissolved form and the protonated sulphonic acids are in equilibrium with the deprotonated sulphinic acids.

As contemplated herein, it is most preferable for M to denote in the Formula (I) M identical or different radicals, selected from a hydrogen atom or an equivalent of an alkali, earth alkali or metal ion from the group of sodium, potassium and ½ zinc.

With respect to the decoloration result, it is advantageous for the cosmetic agent as contemplated herein to additionally contain highly specific sulphonic acids of the Formula (I). It is therefore preferable for the cosmetic agent to contain at least one compound I of the Formula (II), which is selected from the group of $HN(CH_2SO_3Na)_2$, disodium [(sulfinatomethyl)amino]methanesuloinate $HN(CH_2SO_3K)_2$, dipotassium [(sulfinatomethyl)amino] methanesulfonate $HN(CH_2SO_3H)_2$, [(sulfomethyl)amino]methane sulphinic acid $N(CH_2SO_3Na)_3$, trisodium [bis(sulfonatomethyl)amino]methansulfonate $N(CH_2SO_3K)_3$, tripotassium [bis(sulfonatomethyl)amino] methansulfonate $N(CH_2SO_3H)_3$, [Bis(sulfomethyl)amino]methane sulpoinic acid $H_2NCH(CH_3)SO_3Na$, sodium 1-aminoethane-1-sulfonate $H_2NCH(CH_3)SO_3K$, potassium 1-aminoethane-1-sulfonate $H_2NCH(CH_3)SO_3H$, 1-aminoethane-1-sulphonic acid, $HN(CH(CH_3)SO_3Na)_2$, disodium 1-[(1-sulfonatoethyl)amino]ethane-1-sulfonate $HN(CH(CH_3)SO_3K)_2$, dipotassium 1-[(1-sulfnatoethyl)amino]ethane-1-sulfonate $HN(CH(CH_3)SO_3H)_2$, 1-[(1-sulfoethyl)amino]ethane-1-sulphonic acid $N(CH(CH_3)SO_3Na)_3$, trisodium 1-[Bis(1-sulfonatoethyl)amino]ethane-1-sulfonate $N(CH(CH_3)SO_3K)_3$, tripotassium 1-[Bis(1-sulfonatoethyl)amino]ethane-1-sulfonate $N(CH(CH_3)SO_3H)_3$, 1-[bis(1-sulfoothyl)amino]ethane-1-sulphonic acid, as well as the compounds thereof.

The most preferred cosmetic agents in this context are those containing at least one compound II of the Formula (IIa)

$$N(CH_2SO_3Na)_3 \quad (IIa).$$

Use of the aforementioned compounds of the Formula (Ha), which are also referred to as trisodium[bis(sulfinatomethyl)amino]methane sulfonate, in combination with compounds of the Formula (I) and/or (Ia), creates an excellent decoloration effect, particularly on keratinous fibers dyed with oxidative dyes. Moreover, no re-coloration or postdarkening at all occurs after the decoloration process.

The sulphonic acid derivative(s) of the Formula (II) is/are preferably used within specific quantity ranges. As contemplated herein it is therefore advantageous for the at least one compound (I) of the Formula (I) to be contained in a total quantity of from about 0.1 to about 30.0 wt. %, preferably from about 0.2 to about 20.0 wt. %, more preferably from about 0.3 to about 10.0 wt. % and more preferably from about 0.5 to about 6.0 wt. %, relative to the total weight of the cosmetic means. Total quantity means the quantity of all compounds of the Formula (I) contained in the cosmetic agent as contemplated herein.

The preference is therefore for cosmetic agents for the reductive decoloration of dyed keratinous fibers, which contain in a cosmetic carrier a) at least compound of I of the Formula (I)

$$A[(CR^1R^2)SO_2M]_{p,q} \quad (I)$$

wherein

A denotes $N(R^3)_{3-q}$ or $O(R^4)_{2-p}$ $R^1$, $R^2$, $R^4$ denote independently a hydrogen atom or a $C_1$-$C_6$-alkyl group, $R^3$ denotes identical or various radicals selected from a hydrogen atom, a $C_1$-$C_{20}$ alkyl group, a $C_3$-$C_8$ cycloalkyl group, substituted by one to three $C_1$-$C_4$ alkyl radicals if necessary M denotes identical or various residues selected from a hydrogen atom or an equivalent of an alkali, alkali earth or metal ions, more particularly for sodium, potassium, ½ magnesium, ½ calcium, ½ zinc, or an ammonium ion ($NH_4^+$), p denotes the integer 1 or 2, Q denotes the integer 1, 2 or 3, wherein at least one of the radicals $R^1$, $R^2$, $R^4$ denotes a $C_1$-$C_6$ alkyl group, if A denotes $O(R^4{}_{2-p})$, and R3 does not denote a hydrogen atom if q is equal to 1, b) at least one alcohol with from 10 to about 30 hydrogen atoms in a total quantity of from about 0.1 to about 20 wt. %, relative to the total weight of the cosmetic agent, and c) at least compound of I of the Formula (II)

$$A[(CR^1R^2)SO_3M]_{p,q} \qquad (II)$$

wherein A, $R^1$, $R^2$, $R^3$, $R^4$, M, p and q have this same general meaning as in Formula (I), wherein the choice of said variables for a specific case for the compounds of Formulas (I) and (II) does not have to be the same.

In this context, the use of reductive decoloration agents comprising (a) at least one compound of the Formula (Ia)

$$N(CH_2SO_2Na)_3 \qquad (Ia),\text{ and}$$

(b) at least one compound of the Formula (IIa)

$$N(CH_2SO_3Na)_3 \qquad (IIa),$$

is most preferred.

If the reductive decoloration agents as contemplated herein contain both at least one compound I of the Formula (I) and also one compound II of the Formula (II), they are preferably used in specific molar quantity ratios. Therefore, cosmetic agents with a molar ratio of compounds I of the Formula (I) to compounds II of Formula (II) of from about 20:1 to about 1:20 are preferred, from about 10:1 to about 1:10 more preferred and from about 3:1 to about 1:3 most preferred.

According to a most preferred embodiment of the present disclosure, the cosmetic agents exist in the form of an emulsion. Use of the aforementioned compounds of Formulas (I) and/or (Ia), as well as, where applicable, compounds of Formulas (II) and/or (IIa) in combination with the special alcohol b) in the form of an emulsion achieves a significantly reduced unpleasant odor during the reductive decoloration of dyed keratinous fibers compared to the use of the aforementioned compounds in the form of a gel or hydrous solution.

In addition, the cosmetic agent as contemplated herein can contain, as well as compound I of the Formula (I) and where applicable compound (II) of the Formula (II), at least one other reducing agent from the group of sodium dithionit, zinc dithionit, potassium dithionit, sodium sulfite, soldium hydrogen sulfite, potassium sulfite, potassium hydrogen sulfite, ammonium sulfite, sodium thiosulfate, potassium thiosulfate, ammonium thiosulfate, sodium disulfite, potassium disulfite, ammonium disulfite, hydroxymethane sulphinic acid, aminomethan sulphinic acid, cysteine, thio lactic acid, thioglycol acid (alternative name: sulfanyl acetic acid), oxalic acid, oxalic acid and/or ascorbic acid. Reducing agents are chemical compounds that are capable of reducing other chemical compounds by giving up electrons.

Sodium dithionit is an inorganic reducing agent and has the empirical formula $Na_2S_2O_4$ and CAS No. 7775-14-6. Zinc dithionit is an inorganic reducing agent and has the empirical formula $ZnS_2O_4$ and CAS No. 7779-86-4. Potassium dithionit is an inorganic reducing agent and has the empirical formula $K_2S_2O_4$ and CAS No. 14293-73-3. Sodium sulfite is an inorganic reducing agent and has the empirical formula $Na_2SO_3$ and CAS No. 7757-83-7.

Sodium hydrogen sulfite is an inorganic reducing agent and has the empirical formula $NaHSO_3$ and CAS No. 7631-90-5. Sodium hydrogen sulfite is preferably used in the form of a hydrous solution.

Potassium sulfite is an inorganic reducing agent and has the empirical formula $K_2SO_3$ and CAS No. 10117-38-1. Potassium hydrogen sulfite is an inorganic reducing agent and has the empirical formula $KHSO_3$ and CAS No. 7773-03-7. Ammonium sulfite is an inorganic reducing agent and has the empirical formula $(NH_4)_2SO_3$ and CAS No. 10196-04-0. Sodium thiosulfate is an inorganic reducing agent and has the empirical formula $Na_2S_2O_3$ and CAS No. 7772-98-7. Potassium thiosulfate is an inorganic reducing agent and has the empirical formula $K_2S_2O_3$ and CAS No. 10294-66-3. Ammonium thiosulfate is an inorganic reducing agent and has the empirical formula $(NH_4)_2S_2O_3$ and CAS No. 7783-18-8.

Hydroxymethane sulphinic acid is an inorganic reducing agent and has the empirical formula $HO-CH_2-S(O)OH$ and CAS No. 79-25-4. Hydroxymethane sulphinic acid is also referred to as formaldehyde sulfoxylic acid. As contemplated herein, both hydroxymethane sulphinic acid as well as the physiologically tolerated salts thereof, sodium salts and/or zinc salts, for example, can be used.

Amino methane sulphinic acid is an inorganic reducing agent and has the empirical formula $H_2N-CH_2-S(O)OH$ and CAS No. 118201-33-5. As contemplated herein, both amino methane sulphinic acid itself and the physiologically tolerated salts thereof, sodium salt and/or zinc salt, for example, can be used. The use of sodium amino methane sulfinate (sodium salt of amino methane sulphinic acid) and/or zinc amino methane sulfinate (zinc salt of amino methane sulphinic acid) is therefore as contemplated herein.

As contemplated herein cysteine (2-amino-3-sulfanyl propionic acid) means D-cysteine, L-cysteine and/or a mixture of D- and L-cysteine.

Thio lactic acid (2-sulfanylpropionic acid ) means D-thiolactic acid, L-thio-lactic acid and/or a mixture of D- and L-thio lactic acid. The use of both thio lactic acid itself and also thio lactic acid in the form of a physiologically tolerable salt thereof are as contemplated herein. A preferred salt of thio lactic acid is ammonium thiolactate.

Ammonium thiolactate is the ammonium salt of thio lactic acid (i.e. the ammonium salt of 2-sulfanylpropionic acid) with the Formula (III)

$$(III)$$

wherein ammonium thiolactate as contemplated herein means the ammonium salts of D-thio lactic acid, the ammonium salts of L-thio lactic acid and the mixtures thereof.

Thioglycol acid (sulfanyl acetic acid, 2-mercapto-acetic acid) means an organic reducing agent, which has the formula $HS-CH_2-COOH$ and the CAS No. 68-11-1. In the case of thioglycol acid, both the use of thioglycol acid and the use of a physiologically tolerated salt of thioglycol acid is as contemplated herein. Sodium thioglycolate, potassium thioglycolate and/or ammonium thioglycolate, for example, can be used as physiologically tolerated salts of thiolgycol acid. Ammonium thioglylate is a preferred physiologically tolerated salt of thioglycol acid.

Ammonium thioglycolat is the ammonium salt of thiglycol acid (i.e. the ammonium salt of 2-sulfanyl acetic acid) with the Formula (IV)

(IV)

Oxalic acid means the reductive acid HOOC—COOH. Oxalic acid is also referred to as ethane diacide and bears the CAS No. 144-62-7. Alternative names for oxalic acetic acid are oxobutane diacide oxobernstein acid, this acid also have a reductive effect and bears the CAS No. 328-42-7. As contemplated herein, ascorbic acid means in particular (R)-5-[(S)-1,2-dihydroxyethyl]-3,4-dihydroxy-5H-furan-2-on (other alternative names: Vitamin C, L-ascorbic acid) with the CAS No. 50-81-7.

The at least one additional reducing agent from the aforementioned group can be contained in a total quantity of from about 0.1 to about 20.0 wt. %, preferably from about 0.5 to about 10.0 wt. %, more particularly from about 1.0 to about 8.0 wt. %, relative to the total weight of the cosmetic agent.

Moreover, the cosmetic agents as contemplated herein can contain at least one tenside from the group of anionic tensides, amphoteric and/or zwitterionic tensides, non-ionic tensides, cationic tensides and the mixtures thereof. The additional use of tensides effectively stabilizes the emulsion, thereby supporting the reduced unpleasant odor when the cosmetic agent as contemplated herein is applied during the reductive decoloration of dyed keratinous fibers.

Tensides are amphiphilic (bifunctional) compounds, which include at least one hydrophobic and at least one hydrophilic molecular part. The hydrophobic radical is preferably a hydrocarbon chain with from 8 to about 24 carbon atoms, which can be saturated or unsaturated, linear or branched. This $C_8$-$C_{24}$ alkyl chain is most preferably linear. Anionic tensides according to this present disclosure contain at least one anionic group, a carboxylate-, sulfate-, sulfonate- or phosphate group, for example, as well as a lipophilic alkyl group with from 8 to about 30 carbon atoms. The molecule can also contain glycol- or polyglycolether groups, ester-, ether- and amide groups, as well as hydroxyl groups. An anionic tenside as contemplated herein, however, does not contain any cationic groupings, i.e. Zwitterionic tensides do not therefore fall under the definition of anionic tensides as contemplated herein.

Typical examples of anionic tensides are alkyl benzol sulfonates, alkansulfonates, olefinsulfonates, alkylethersulfonates, glycerinethersulfonates, α-methylestersulfonates, sulfo fatty acids, alkyl sulfates, fatty alcohol ethersulfates, glycerinethersulfates, hydroxy mixed ethersulfates, monoglycerid(ether)sulfates, fatty acid amid(ether)sulfates, mono- and dialkyl sulfosuccinates, mono- and dialkylsulfosuccinamates, sulfotriglycerides, amide soaps, ether carbon acids and the salts thereof, fatty acid isethionates, fatty acid sarcosinates, fatty acid taurides, acyllactylates, acyltartrates, acylglutamates, acylaspartates, alkyloligoglucosidsulfates, protein fatty acid condensate (more particularly wheat-based plant products) and alkyl(ether) phosphates. Insofar as anionic tensides contain polyglycolether chains, they can have a conventional, preferably however a constricted, homologous distribution.

Examples of anionic tensides as contemplated herein are, in each case in the form of sodium, potassium and ammonium, as well as the mono-, di- and trialkanolammonium salts with from 2 to 4 carbon atoms in the alkanol group, linear and branched fatty acids with from 8 to about 30 carbon atoms (soap), Ether carbon acids of Formula R5-O-(CH2-CH2O)x-CH2-COOH, in which R5 is a linear alkyl group with from 8 to about 30 carbon atoms and x=about 0 or from about 1 to about 16, Acylsarcosides with from 8 to about 24 carbon atoms in the acyl group, Acyltauride with from 8 to about 24 carbon atoms in the acyl group, Acylisethionates with from 8 to about 24, more particularly from 12 to 18, carbon atoms in the acyl group, which made accessible through the esterification of fatty acids with the sodium salt of the 2-hydroxyethane sulfonic acid (isethionic acid), sulfobernstein acid mono- and -dialkylesters with from 8 to about 24, preferably from 12 to 18, carbon atoms in the alkyl group and sulfobernstein acid monoalkylpolyoxyethylesters with from 8 to about 24, preferably from 12 to 18, carbon atoms in the alkyl group and from 1 to 6 oxyethyl groups, linear alkansulfonates with from 8 to about 24 carbon atoms, linear alpha olefin sulfonates with from 8 to about 24 carbon atoms, alpha-sulfo fatty acid methyl esters of fatty acids with from 8 to about 30 carbon atoms, alkylsulfates and alkylpolyglykolethersulfates of formula $R^6$—$O(CH_2$—$CH_2O)_x$—$OSO_3H$, in which $R^6$ is preferably a linear alkyl group with from 8 to about 30 carbon atoms and x=0 or from 1 to 12, hydroxy sulfonate correspond substantially to at least one of the following two formulas or the mixtures thereof, as well as the salts thereof, $CH_3$—$(CH_2)_y$—$CHOH$—$(CH_2)_a$—$(CH$—$SO_3M)$-$(CH_2)_z$—$CH_2$—$O$—$(CnH_{2n}O)_x$—$H$, and/or $CH_3$—$(CH_2)_y$—$(CH$-$SO_3M)$-$(CH_2)_a$—$CHOH$—$(CH_2)_z$—$CH_2$—$O$—$(C_nH_{2n}O)_x$—$H$, wherein in both formulas y and z=0 or an integer from 1 to 18, a=0, 1 or 2 and the sum total (y+z+a) an integer from 12 to 18, x=0 or an integer from 1 to 30 and n is an integer from 2 to 4, and also M=H or alkali-, more particularly sodium, potassium, lithium, earth alkali-, more particularly magnesium, calcium, zinc and/or an ammonium ion, which can be substituted, in particular mono-, di-, tri- or tetraammonium ions with $C_1$ to $C_4$ alkyl-, alkenyl- or aryl radicals, sulfated hydroxyalkylpolyethylene- and/or hydroxyalkylenpropylenglykolether of the Formula $R^7$—$(CHOSO_3M)$-$CHR^9$—$(OCHR^{10}$—$CH_2)_n$—$OR^8$ with $R^7$, a linear alkyl radical with from 1 to about 24 carbon atoms, $R^8$ is a linear or branched, saturated alkyl radical with from 1 to about 24 carbon atoms, $R^9$ is hydrogen or a linear alkyl radical with from 1 to about 24 carbon atoms, $R^{10}$ is hydrogen or a methyl radical and M is hydrogen, ammonium, alkyl ammonium, alkanolammonium, wherein the alkyl- and alkanol radicals each have from 1 to 4 carbon atoms, or a metal atom selected from lithium, sodium, potassium, calcium or magnesium and n is an integer in the range of from 0 to 12, and the total number of carbon atoms contained in $R^1$ and $R^3$ is from 2 to about 44, Sulfonates of unsaturated fatty acids with from 8 to about 24 carbon atoms and from 1 to 6 double bonds, esters of tartaric and citric acid with alcohols, which constitute binding agents from approximately 2 to 15 molecules of ethylenoxide and/or propylenoxide of fatty alcohols with from 8 to about 22 carbon atoms, alkyl- and/or alkenyletherphosphates of the Formula $R^{11}(OCH_2CH_2)_n$—O—(PO—OX)—$OR^{12}$, in which $R^{11}$ preferably denotes an aliphatic hydrocarbon radical with from 8 to about 30 carbon atoms, $R^{12}$ denotes hydrogen, a radical $(CH_2CH_2O)_nR^{12}$ o X, n denotes integers from 1 to 10 and X denotes hydrogen, an alkali- or earth alkali metal or $NR^{13}R^{14}R^{15}R^{16}$, with $R^{13}$ to $R^{16}$ denote independently hydrogen or a $C_1$-$C_4$ hydrocarbon residue, sulfated fatty acid alkylenglykolesters of the Formula $R^{17}CO(AlkO)_nSO_3M$, in which $R^{17}CO$ denotes a linear or branched, aliphatic, saturated and/or unsaturated acyl radical with from 6 to about 22 carbon atoms, Alk denotes $CH_2CH_2$, $CHCH_3CH_2$ and/or $CH_2CHCH_3$, n denotes integers from 0.5 to 5 and M denotes a metal, such as an alkali metal, more particularly sodium, potassium, lithium, earth alkali metal, more particularly magnesium, calcium, zinc, or ammonium ion, such as $^+NR^{13}R^{14}R^{15}R^{16}$, with $R^{13}$ to $R^{16}$ denoting independently hydrogen or a $C_1$-$C_4$ hydrocarbon radical, monoglyceridsulfates and monoglyceridethersulfates of the Formula $R^{18}OC$—$(OCH_2CH_2)_x$—$OCH_2$—[CHO$(CH_2CH_2O)_yH$]—$CH_2O(CH_2CH_2O)_z$—$SO_3X$, in which $R^{18}CO$ denotes a linear or branched acyl radical with from 6 to about 22 carbon atoms, more particularly a linear acyl radical with from 8 to 18 carbon atoms, x, y and z in total denotes 0 or integers from 1 to 30, more preferably 2 to 10, and X denotes an alkali- or earth alkali metal, amidethercarbonic acids of the Formula $R^{19}$—CO—$NR^{20}$—$CH_2CH_2$—O—$(CH_2CH_2O)_nCH_2COOM$, with $R^{19}$ as straight-chained or branched alkyl- or alkenyl radical with a number of carbon atoms in the chain from 2 to about 30, n denotes an integer from 1 to 20 and $R^{20}$ denotes hydrogen, a methyl-, ethyl-, propyl-, isopropyl-, n-butyl-, t-butyl- or iso-butyl radical and M stands for hydrogen or a metal such as an alkali metal, more particularly sodium, potassium, lithium, earth alkali metal, more particularly magnesium, calcium, zinc, or an ammonium ion, such as $^+NR^{13}R^{14}R^{15}R^{16}$, with $R^{13}$ to $R^{16}$ denoting independently hydrogen or a $C_1$-$C_4$ hydrogen radical. Such products can be obtained from the company Chem-Y, for example, under the product designation Akypo®, and acylglutamates of the Formula XOOC—$CH_2CH_2CH(C$(NH)$OR^{21}$)—COOX, in which $R^{21}CO$ denotes a linear or branched acyl radical with from 6 to about 22 carbon atoms and 0 and/or 1, 2 or 3 double bonds and X for hydrogen, an alkali and/or earth alkali metal, ammonium, alkyl ammonium, alkanolammonium or glucammonium.

The cosmetic agents as contemplated herein can likewise contain an amphoteric and/or zwitterionic tenside. In the case of the zwitterionic tensides, the hydrophilic molecule comprises a zwitterionic structural unit, i.e. a structural unit comprising both a cationically-charged and also an anionically-charged molecule. As contemplated herein, particularly suitable zwitterionic tensides are exemplified in that they have a cationically-charged molecule in the form of a quaternary ammonium group and their anionic molecule exists in the form of a $SO_3$ or COO grouping. An ammonium group is quaternary when a type $(R_aR_bR_cR_dN)^+$ grouping exists, i.e. when all four H-atoms of the $NH_4$ ion from which the quaternary ammonium group is derived, is replaced by organic radicals R (and/or $R_a$ to $R_d$). The $SO_3$ grouping of the zwitterionic tenside can be bound directly to a carbon atom. In this case, the anionic part of the zwitterionic compound is a deprotonated sulfonic acid grouping.

Particularly suitable zwitterionic tensides include betaine, N-alkyl-N,N-dimethylammonium-glycinate, N-acyl-aminopropyl-N,N-dimethylammoniumglycinate, and 2-alkyl-3-carboxymethyl-3-hydroxyethyl-imidazoline, N-alkylglycine, N-alkyl propionic acids, N-alkylamino butyric acids, N-alkyliminodipropionic acids, N-hydroxyethyl-N-alkylamidopropylglycines, N-alkyltaurines, N-alkylsarcosines, 2-alkylaminopropionic acids and alkylamino acetic acids. Particularly preferred amphoteric tensides are N-cocosalkylaminopropionate, cocosacylaminoethylaminopropionate and $C_{12}$-$C_{18}$ acylsarcosin.

It has also proved advantageous for the agent to contain other, non-ionogenic surfactants. Preferred non-ionic surfactants are alkyl polyglycosides as well as alkylene oxide binding agents to fatty alcohols, fatty acids and fatty acid glycerides with from 2 to about 50 moles of ethylene oxide per mole of fatty alcohol or fatty acid. Fatty acid esters of ethoxylated glycerine are also advantageous as non-ionic tensides. The most preferred embodiment is the cosmetic agent containing as a non-ionic tenside an ethoxylated castor oil with from 2 to about 50 mol ethylenoxyide per mol of fatty acid or an ethoxylated, hydrated castor oil with from 2 to about 50 mol ethylenoxyide per mol of fatty acid. The use of PEG-40 Castor Oil is most preferred in this context.

The agents as contemplated herein can contain at least one cationic tenside. Cationic tensides are tensides containing exclusively a temporarily or permanently positive group. Temporaryily cationic groups are those that have a cationic group depending on the pH value of the cosmetic agent as contemplated herein. Permanently cationic groups are those that are cationic regardless of the pH value of the cosmetic agent as contemplated herein. Examples are groups containing a quaternary nitrogen atom.

Typical cationic tensides are

Quaternary ammonium bonds, which can carry, as hydrophobic radicals, one or two alkyl chains with a chain length of from 8 to about 28 carbon atoms quaternay phosphonium salts, substituted with one or more alkyl chains with a chain length of from 8 to about 28 C-atoms or Tertiary sulfonium salts.

Moreover, the cationic charging can also occur in the form of an onium structure component of a heterocyclical ring (e.g. of an imidazolium ring or a pyridinium ring).

In addition to the functional unit carried by the cationic charge, the cationic tenside can also contain other uncharged functional groups, which is the case with esterquats, for example. As contemplated herein, preferred cationic tensides are of the type of quaternary ammonium compounds, eterquats and amidoamines. Preferred quaternary ammonium compounds are ammonium compounds and ammonium halogenides, more particularly chlorides and bromides, such as alkyltrimethylammoniumchlorides, dialkyldimethylammoniumchlorides and trialkylmethyl-ammoniumchlorides, e.g. cetyltrimethylammoniumchloride, stearyltrimethylammoniumchloride, distearyldimethylammoniumchloride, lauryldimethylammoniumchlorids, lauryldimethylbenzyl-ammoniumchloride and tricetylmethyl-ammoniumchloride, as well as the imidazolium compounds known under the INCI trade names of Quaternium-27 and Quaternium-83. The long alkyl chains of the aforementioned tensides preferably have from 10 to 18 carbon atoms.

Esterquats are known substances containing both at least one ester function and at least quaternary ammonium group as the structural element. Preferred esterquats are quaternated ester salts of fatty acids with triethanolamine, quaternated ester salts of fatty acids with diethanolalkyl amines and quaternated ester salts of fatty acids with 1,2-dihydroxypropyldialkylamines. The alkylamidoamines are usually produced through the amidation of natural or synthetic fatty acids and fatty acid molecules with dialkylaminoamines. A most preferred compound from this substance group as contemplated herein is the stearamidopropyldimethylamine commercially available under the trade name of Tegoamid(r) S 18. As contemplated herein, the quaternized protein hydrolysates can also be used.

The anionic, amphoteric and/or zwitterionic, non-ionic and cationic tensides can be contained in a total quantity of from about 0.01 to about 15 wt. %, preferably from about 0.1 to about 10 wt. %, more preferably from about 0.2 to about 5.0 wt. %, most preferably from about 0.3 to about 2.0 wt. %, relative to the total weight of the cosmetic agent.

The cosmetic agents as contemplated herein can also contain at least one polyol. A polyol is a compound having at least two aliphatic (i.e. non- phenolic) OH groups.

Preferred cosmetic agents are therefore exemplified in that the contain at least one polyol from the group of ethylengylcol (1,2-ethandiol), 1,2-propandiol, 1,3-propandiol, 1,2-butandiol, 1,3-butandiol, 1,4-butandiol, 1,2-pentantiol, 1,3-pentantiol, 1,4-pentantiol, 1,5-pentantiol, 1,2-hexandiol, 1,3-hexandiol, 1,4-hexantiol, 1,5-hexandiol, 1,6-hexandiol, polyethylenglycol, polypropylenglycol, as well as the mixtures thereof.

The agents as contemplated herein preferably contain polyols in a total quantity of from about 0.01 to about 5.0 wt. %, preferably from about 0.1 to about 4.0 wt. %, more preferably from about 0.2 to about 3.0 wt. %, most preferably from about 0.3 to about 2.5 wt. %, relative to the total weight of the cosmetic agent.

Preferably, the cosmetic means as contemplated herein are formulated as free-flowing preparations. The cosmetic agents must be formulated in such a manner that they can be readily applied and distributed at the place of use on the one hand, but on the other are adequately viscous such that they remain at the site of action and do not run during the exposure time.

According to the present disclosure, therefore, it is preferable for the cosmetic agents as contemplated herein to contain at least one thickening agent, selected from the group of anionic synthetic polymers, cationic synthetic polymers, non-ionic guargums, scleroglucangums or xanthangums, rubber arabicum, Carrageen rubber, Agar-Agar, locust bean gum, pectines, alginates, starches, celluloses and cellulose derivatives, non-ionic synthetic polymers, as well as the mixtures thereof.

It has proven advantageous in this context if the thickening agent is contained in a total quantity of from about 0.0005 to about 5.0 wt. %, preferably from about 0.001 to about 1.0 wt. %, more preferably from about 0.005 to about 0.5 wt. %, most preferably from about 0.01 to about 0.3 wt. %, relative to the total weight of the cosmetic agent.

The cosmetic agents as contemplated herein preferable have a certain viscosity to guarantee good distributability on the one hand, and on the other to prevent the agent from running out of the hair. As contemplated herein, it is therefore preferable for the cosmetic agent to have a viscosity, measured at about 20° C using a Brookfield rotation viscosity meter, spindle about 5, about 20 rpm, of from about 100 to about 100,000 mPa·s, preferably from about 300 to about 80,000 mPa·s, more preferably from about 500 to about 60.000 mPa·s, even more preferably from about 700 to about 40,000 mPa·s, and most preferably from about 1,000 to about 30,000 mPa·s.

The decoloration effect of the cosmetic agent as contemplated herein can be optimized by setting certain pH values. A better decoloration effect was observed at acid pH values in the range of from about 0.5 to about 5.0. As contemplated herein, it is therefore preferable for the cosmetic agent to have a pH value, measured at about 20° C, from about pH 0.5 to about pH 5.0, more preferably from about pH 0.6 to about pH 4.5, and most preferably from about pH 1.0 to about pH 4.0. The pH value is adjusted through the use of acids. According to the present disclosure, the preference is for at least one acid from the group of citric acid, tartaric acid, malic acid, lactic acid, acetic acid, sulphuric acid, hydrochloric acid, phosphoric acid, methane sulfonic acid, benzoic acid, malonic acid, oxalic acid, pyruvic acid, oxalocetic acid (oxobutanic acid), oxal acetic acid diester, 1-hydroxyethane-1,1-diphosphonic acid, as well as the mixtures thereof.

The tables below show most preferred embodiments of the cosmetic agents as contemplated herein, all agents existing in the form of emulsions and having a pH value of from about 1.0 to about pH 4.0 (measured at about 20° C) (all values in wt. %, unless otherwise specified):

|  | AF 1 | AF 2 | AF 3 | AF4 |
| --- | --- | --- | --- | --- |
| Compound I Formula (I) | 0.1 to 30.0 | 0.2 to 20.0 | 0.3 to 10.0 | 0.5 to 6.0 |
| Alcohol b) with 10 to 30 C-atoms | 0.5 to 18 | 1.0 to 15 | 1.2 to 12 | 1.5 to 10 |
| Cosmetic carrier | Ad 100 | Ad 100 | Ad 100 | Ad 100 |

|  | AF 5 | AF 6 | AF 7 | AF8 |
| --- | --- | --- | --- | --- |
| Compound I Formula (Ia) | 0.1 to 30.0 | 0.2 to 20.0 | 0.3 to 10.0 | 0.5 to 6.0 |
| Alcohol b) with 10 to 30 C-atoms | 0.5 to 18 | 1.0 to 15 | 1.2 to 12 | 1.5 to 10 |
| Cosmetic carrier | Ad 100 | Ad 100 | Ad 100 | Ad 100 |

|  | AF 9 | AF 10 | AF 11 | AF12 |
| --- | --- | --- | --- | --- |
| Compound I Formula (Ia) | 0.1 to 30.0 | 0.2 to 20.0 | 0.3 to 10.0 | 0.5 to 6.0 |
| Alcohol b) with 10 to 30 C-atoms[1] | 0.5 to 18 | 1.0 to 15 | 1.2 to 12 | 1.5 to 10 |
| Cosmetic carrier | Ad 100 | Ad 100 | Ad 100 | Ad 100 |

|  | AF 13 | AF 14 | AF 15 | AF16 |
| --- | --- | --- | --- | --- |
| Compound I Formula (Ia) | 0.1 to 30.0 | 0.2 to 20.0 | 0.3 to 10.0 | 0.5 to 6.0 |
| Mixture from cetyl alcohol and stearyl alcohol | 0.5 to 18 | 1.0 to 15 | 1.2 to 12 | 1.5 to 10 |
| Cosmetic carrier | Ad 100 | Ad 100 | Ad 100 | Ad 100 |

|  | AF 17 | AF 18 | AF 19 | AF 20 |
|---|---|---|---|---|
| Compound I Formula (Ia) | 0.1 to 30.0 | 0.2 to 20.0 | 0.3 to 10.0 | 0.5 to 6.0 |
| Alcohol b) with 10 to 30 C-atoms | 0.5 to 18 | 1.0 to 15 | 1.2 to 12 | 1.5 to 10 |
| Xanthan | 0.0005 to 5.0 | 0.001 to 1.0 | 0.005 to 0.5 | 0.01 to 0.3 |
| Cosmetic carrier | Ad 100 | Ad 100 | Ad 100 | Ad 100 |

|  | AF 21 | AF 22 | AF 23 | AF 24 |
|---|---|---|---|---|
| Compound I Formula (Ia) | 0.1 to 30.0 | 0.2 to 20.0 | 0.3 to 10.0 | 0.5 to 6.0 |
| Alcohol b) with 10 to 30 C-atoms | 0.5 to 18 | 1.0 to 15 | 1.2 to 12 | 1.5 to 10 |
| Xanthan | 0.0005 to 5.0 | 0.001 to 1.0 | 0.005 to 0.5 | 0.01 to 0.3 |
| Tenside[2)] | 0.01 to 15 | 0.1 to 10 | 0.2 to 5.0 | 0.3 to 2.0 |
| Cosmetic carrier | Ad 100 | Ad 100 | Ad 100 | Ad 100 |

|  | AF 25 | AF 26 | AF 27 | AF 28 |
|---|---|---|---|---|
| Compound I Formula (Ia) | 0.1 to 30.0 | 0.2 to 20.0 | 0.3 to 10.0 | 0.5 to 6.0 |
| Alcohol b) with 10 to 30 C-atoms | 0.5 to 18 | 1.0 to 15 | 1.2 to 12 | 1.5 to 10 |
| Xanthan | 0.0005 to 5.0 | 0.001 to 1.0 | 0.005 to 0.5 | 0.01 to 0.3 |
| Tenside[2)] | 0.01 to 15 | 0.1 to 10 | 0.2 to 5.0 | 0.3 to 2.0 |
| Reducing agent[3)] | 0.05 to 5.0 | 0.1 to 4.0 | 0.2 to 3.0 | 0.3 to 2.0 |
| Cosmetic carrier | Ad 100 | Ad 100 | Ad 100 | Ad 100 |

|  | AF 29 | AF 30 | AF 31 | AF 32 |
|---|---|---|---|---|
| Compound I Formula (Ia) | 0.1 to 30.0 | 0.2 to 20.0 | 0.3 to 10.0 | 0.5 to 6.0 |
| Mixture of cetyl alcohol and stearyl alcohol | 0.5 to 18 | 1.0 to 15 | 1.2 to 12 | 1.5 to 10 |
| Xanthan | 0.0005 to 5.0 | 0.001 to 1.0 | 0.005 to 0.5 | 0.01 to 0.3 |
| Tenside[2)] | 0.01 to 15 | 0.1 to 10 | 0.2 to 5.0 | 0.3 to 2.0 |
| Reducing agent[3)] | 0.05 to 5.0 | 0.1 to 4.0 | 0.2 to 3.0 | 0.3 to 2.0 |
| Cosmetic carrier | Ad 100 | Ad 100 | Ad 100 | Ad 100 |

|  | AF 33 | AF 34 | AF 35 | AF 36 |
|---|---|---|---|---|
| Compound I Formula (I) | 0.1 to 30.0 | 0.2 to 20.0 | 0.3 to 10.0 | 0.5 to 6.0 |
| Alcohol b) with 10 to 30 C-atoms | 0.5 to 18 | 1.0 to 15 | 1.2 to 12 | 1.5 to 10 |
| Compound II Formula (II) | 0.1 to 30.0 | 0.2 to 20.0 | 0.3 to 10.0 | 0.5 to 6.0 |
| Cosmetic carrier | Ad 100 | Ad 100 | Ad 100 | Ad 100 |

|  | AF 37 | AF 38 | AF 39 | AF 40 |
|---|---|---|---|---|
| Compound I Formula (Ia) | 0.1 to 30.0 | 0.2 to 20.0 | 0.3 to 10.0 | 0.5 to 6.0 |
| Alcohol b) with 10 to 30 C-atoms | 0.5 to 18 | 1.0 to 15 | 1.2 to 12 | 1.5 to 10 |
| Compound I Formula (IIa) | 0.1 to 30.0 | 0.2 to 20.0 | 0.3 to 10.0 | 0.5 to 6.0 |
| Cosmetic carrier | Ad 100 | Ad 100 | Ad 100 | Ad 100 |

|  | AF 41 | AF 42 | AF 43 | AF 44 |
|---|---|---|---|---|
| Compound I Formula (Ia) | 0.1 to 30.0 | 0.2 to 20.0 | 0.3 to 10.0 | 0.5 to 6.0 |
| Alcohol b) with 10 to 30 C-atoms [1)] | 0.5 to 18 | 1.0 to 15 | 1.2 to 12 | 1.5 to 10 |
| Compound I Formula (IIa) | 0.1 to 30.0 | 0.2 to 20.0 | 0.3 to 10.0 | 0.5 to 6.0 |
| Cosmetic carrier | Ad 100 | Ad 100 | Ad 100 | Ad 100 |

|  | AF 45 | AF 46 | AF 47 | AF 48 |
|---|---|---|---|---|
| Compound I Formula (Ia) | 0.1 to 30.0 | 0.2 to 20.0 | 0.3 to 10.0 | 0.5 to 6.0 |

-continued

|  | AF 45 | AF 46 | AF 47 | AF 48 |
|---|---|---|---|---|
| Mixture from cetyl alcohol and stearyl alcohol | 0.5 to 18 | 1.0 to 15 | 1.2 to 12 | 1.5 to 10 |
| Compound I Formula (IIa) | 0.1 to 30.0 | 0.2 to 20.0 | 0.3 to 10.0 | 0.5 to 6.0 |
| Cosmetic carrier | Ad 100 | Ad 100 | Ad 100 | Ad 100 |

|  | AF 49 | AF 50 | AF 51 | AF 52 |
|---|---|---|---|---|
| Compound I Formula (Ia) | 0.1 to 30.0 | 0.2 to 20.0 | 0.3 to 10.0 | 0.5 to 6.0 |
| Alcohol b) with 10 to 30 C-atoms | 0.5 to 18 | 1.0 to 15 | 1.2 to 12 | 1.5 to 10 |
| Compound I Formula (IIa) | 0.1 to 30.0 | 0.2 to 20.0 | 0.3 to 10.0 | 0.5 to 6.0 |
| Xanthan | 0.0005 to 5.0 | 0.001 to 1.0 | 0.005 to 0.5 | 0.01 to 0.3 |
| Cosmetic carrier | Ad 100 | Ad 100 | Ad 100 | Ad 100 |

|  | AF 53 | AF 54 | AF 55 | AF 56 |
|---|---|---|---|---|
| Compound I Formula (Ia) | 0.1 to 30.0 | 0.2 to 20.0 | 0.3 to 10.0 | 0.5 to 6.0 |
| Alcohol b) with 10 to 30 C-atoms | 0.5 to 18 | 1.0 to 15 | 1.2 to 12 | 1.5 to 10 |
| Compound I Formula (IIa) | 0.1 to 30.0 | 0.2 to 20.0 | 0.3 to 10.0 | 0.5 to 6.0 |
| Xanthan | 0.0005 to 5.0 | 0.001 to 1.0 | 0.005 to 0.5 | 0.01 to 0.3 |
| Tenside [2] | 0.01 to 15 | 0.1 to 10 | 0.2 to 5.0 | 0.3 to 2.0 |
| Cosmetic carrier | Ad 100 | Ad 100 | Ad 100 | Ad 100 |

|  | AF 57 | AF 58 | AF 59 | AF 60 |
|---|---|---|---|---|
| Compound I Formula (Ia) | 0.1 to 30.0 | 0.2 to 20.0 | 0.3 to 10.0 | 0.5 to 6.0 |
| Alcohol b) with 10 to 30 C-atoms | 0.5 to 18 | 1.0 to 15 | 1.2 to 12 | 1.5 to 10 |
| Compound I Formula (IIa) | 0.1 to 30.0 | 0.2 to 20.0 | 0.3 to 10.0 | 0.5 to 6.0 |
| Xanthan | 0.0005 to 5.0 | 0.001 to 1.0 | 0.005 to 0.5 | 0.01 to 0.3 |
| Tenside [2] | 0.01 to 15 | 0.1 to 10 | 0.2 to 5.0 | 0.3 to 2.0 |
| Reducing agent [3] | 0.05 to 5.0 | 0.1 to 4.0 | 0.2 to 3.0 | 0.3 to 2.0 |
| Cosmetic carrier | Ad 100 | Ad 100 | Ad 100 | Ad 100 |

|  | AF 61 | AF 62 | AF 63 | AF 64 |
|---|---|---|---|---|
| Compound I Formula (Ia) | 0.1 to 30.0 | 0.2 to 20.0 | 0.3 to 10.0 | 0.5 to 6.0 |
| Mixture from cetyl alcohol and stearyl alcohol | 0.5 to 18 | 1.0 to 15 | 1.2 to 12 | 1.5 to 10 |
| Compound I Formula (IIa) | 0.1 to 30.0 | 0.2 to 20.0 | 0.3 to 10.0 | 0.5 to 6.0 |
| Xanthan | 0.0005 to 5.0 | 0.001 to 1.0 | 0.005 to 0.5 | 0.01 to 0.3 |
| Tenside [2] | 0.01 to 15 | 0.1 to 10 | 0.2 to 5.0 | 0.3 to 2.0 |
| Reducing agent [3] | 0.05 to 5.0 | 0.1 to 4.0 | 0.2 to 3.0 | 0.3 to 2.0 |
| Cosmetic carrier | Ad 100 | Ad 100 | Ad 100 | Ad 100 |

Alcohol b) with from about 10 to about 30 C-atoms selected from the group of 1-decanol, laurylalcohol, myristyl alcohol, cetylalcohol, stearyl alcohol, arachidylalcohol, behenylalcohol, lignocerylalcohol, cerylalcohol, montanylalcohol, as well as the mixtures thereof

[2] Mixture from cocamidopropylbetain, sodium cetearyl sulfate and PEG-40 Castor Oil

[3] Reducing agent is selected from the group of malonic acid, oxalic acid, oxalic acid esters, ascorbic acids, as well as the mixtures thereof, more particularly oxalic acid The aforementioned most preferred embodiments AF1 to AF64 of the cosmetic agent as contemplated herein are exemplified by an outstanding decoloration of oxidatively colored keratinous fibers, wherein the decoloration effect is long-lasting without any post darkening. Moreover, the application of said decoloration emulsions reduces the unplesant odor during the decoloration process compared to decoloration agents known from the prior art.

The cosmetic agents according to the present disclosure can also be produced immediately prior to application from two or more separately packaged compositions. According to the present disclosure, this is advantageous since the compounds of the Formulas (I) and/or (Ia) and (II) and/or (IIa) have a higher storage stability at alkali pH values, with the decoloration process, however, favoring an acid environment. For these reasons, it is advantageous for decoloration agents stored at an alkali pH to be brought to an acid pH shortly before use. The acidification of previously alkali decoloration agents shortly before use can be realized by mixing two different agents, wherein the alkali first agent described above is mixed with a further agent which contains one or more acids.

The two components required to produce the ready-to-use agent are practically provided to the user in the form of a kit (i.e. a kit-of-parts), which comprises at least two preparations (1) and (2) packaged separately from one another. The first preparation (1) contains, in a cosmetic carrier, at least one compound I of the Formula (I), and where applicable at least one compound II of the Formula (II), as defined above, whereas the second preparation (2) comprises the acids required to produce the pH value. The ready-to-use decoloration agent can be produced by mixing preparations (1) and (2).

A second subject matter of the present disclosure is therefore a kit-of-parts for the reductive decoloration of dyed keratinous fibers, comprising at least two preparations (1) and (2) packaged separately from one another, wherein the first preparation (1) in a cosmetic carrier contains at least one compound I of the Formula (I), and where applicable at least one compound II of the Formula (II), as defined in the first subject matter of the present disclosure, and the second preparation (2) contains at least one inorganic and/or organic acid, wherein preparation (1) and/or preparation (2) contains at least one alcohol with from 10 to about 30 carbon atoms in a total quantity of from about 0.1 to about 20 wt. %, relative to the total weight of preparation (2).

The decoloration agent producible from the kit-of-parts as contemplated herein leads to improved decoloration of dyed keratinous fibers. Moreover, no post-darkening or re-coloration occurs after the decoloration process. In addition, the decoloration agents producible from the kit-of-parts can significantly reduce the unpleasant odor compared to decoloration agents known from the prior art.

As contemplated herein, the first preparation (1) has a specific water content and an alkali pH value, in order to increase the stability of compound I of the Formula (I) and, where applicable, of compound II of the Formula (II). Therefore, it is advantageous for the first preparation (1) to have a pH value, measured at about 20° C, from about pH 7.5 to about pH 12.0, preferably from about pH 8.0 to about pH 11.5, more preferably from about pH 8.5 to about pH 11.0, most preferably from about pH 9.0 to about pH 10.5, and a water content from about 5.0 to about 99.0 wt. %, preferably from about 15.0 to about 98.0 wt. %, most preferably from about 50 to about 98 wt. %, relative to the total weight of the preparation (1)

The alkalizing agents which can be used to set the pH value of the first preparation (1) can be selected from the group of ammoniac, alkanolamines, basic aminco acids, as well as inorganic alkalizing agents such as (earth-)alkali metal hydroxides, (earth-)alkali metal lmetasilicates, (earth-) alkali metal phosphates and (earth-)alkali metal hydrogen phosphates. Suitable inorganic alkalizing agents are sodium hydroxide, sodium hydroxide, sodium silicate and sodium metasilicate. Organic alkalizing agents usable as contemplated herein are can be selected from monoethanolamine, 2-amino-2-methylpropanol and triethanolamine. The basic amino acids that can be used as alkalizing agents are preferably can be selected from the group formed of arginine, lysine, ornithine, and histidine.

The use of one or more alkalizing agents from the group of sodium hydroxide, potassium hydroxide, ammonia, monoethanolamine and/or arginine is more preferred. The use of sodium hydroxide and/or potassium hydroxide is most preferred.

According to the present disclosure, therefore, it is preferable for the first preparation (1) to contain at least one alkalizing agent from the group of sodium hydroxide, potassium hydroxide, ammonia, monoethanolamine and/or arginine, most preferably sodium hydroxide and/or potassium hydroxide.

The at least one compound I of the Formula (I) and, where applicable, the at least one compound II of Formula (II) are preferably contained in a total quantity in the first preparation. Advantageously, the preparation (1) therefore contains at least one compound I of the Formula (I), as well as, where applicable, at least one compound II of the Formula (II) in a total quantity of from about 0.6 to about 60 wt. %, preferably from about 0.9 to about 50 wt. %, more preferably from about 1.5 to about 40 wt. %, most preferably from about 2.0 to about 30 wt. %, relative to the total weight of the preparation (1). Total quantity means the quantity of all compounds I of the Formula (I), as well as all compounds II of the Formula (II) contained in the composition (1).

The second preparation (2) preferably has an acid pH value, in order to guarantee that the decoloration agent producible from the kit-of-parts is set to an acid pH value. Due to the instability of the reducing agent in an acid environment, the second preparation (2) therefore preferably contains no compound I of the Formula (I), no compound II of the Formula (II) and no other reducing agents stated under the first subject matter of the present disclosure. In order to set an acid pH value, the second preparation (2) contains at least one acid. According to the present disclosure, organic acids are preferably used. According to the present disclosure, it is therefore preferable for the second preparation (2) to contain at least one organic acid, selected from the group of citric acid, tartaric acid, malic acid, lactic acid, acetic acid, sulphuric acid, hydrochloric acid, phosphoric acid, methane sulfonic acid, benzoic acid, malonic acid, oxalic acid, pyruvic acid, oxalocetic acid (oxobutanic acid), oxal acetic acid ester, 1-hydroxyethane-1,1-diphosphonic acid, as well as the mixtures thereof.

If is also preferable for the second preparation (2) to have a pH value, measured at about 20° C, from about pH 0.1 to about pH 4.0, preferably from about pH 0.2 to about pH 3.0, more preferably from about pH 0.5 to about pH 2.0, and a water content from about 5.0 to about 99 wt. %, relative to the total weight of the second preparation (2).

A particularly high reduction of the unpleasant odor is achieved if an emulsion is used as the second preparation (2). As contemplated herein, therefore, the second preparation (2) exists in the form of an emulsion.

To stabilize the emulsion, it is advantageous for the second preparation (2) to have at least one tenside from the group of anionic tensides, amphoteric and/or zwitterionic tensides, catioic tensides, as well as the mixtures thereof. With respect to the usable tensides, reference is made to the statements above regarding the first subject matter of the present disclosure. The anionic, amphoteric and/or zwitterionic, non-ionic and cationic tensides can be contained in a total quantity of from about 0.01 to about 40 wt. %, preferably from about 0.1 to about 30 wt. %, more preferably from about 0.2 to about 20 wt. %, most preferably from about 0.3 to about 10 wt. %, relative to the total weight of the second preparation (2).

As described above, the ready-to-use decoloration agent is preferably produced by mixing two preparations (1) and (2). In principle, the preparations (1) and (2) can be mixed in various mixing ratios, such as (1)/(2) from about 20:1 to about 1:20. The preparations (1) and (2) are preferably mixed with one another in a mixing ratio of from about 1:10 to about 10:1, more preferably from about 1:4 to about 4:1. The mixing ratios indicate the ratio of the total quantities of the preparations (1) and (2) relative to one another.

The preparations (1) and (2) are packaged separately from one another and can exist packaged in a container suitable for the purpose. Suitable containers include glass, or more particularly, plastic bottles, jars, tubes or other suitable containers.

To produce the ready-to-use mixture, the first preparation (1) from Container (C1) can be completely transferred to Container (C2)—which already contains the second preparation (2). In this case, the size of Container (C2) is selected such that Container (C2) can receive the total quantity of the preparations (1) and (2) and also allows the two preparations (1) and (2) to be mixed by shaking or stirring, for example.

Likewise, the mixture can be produced by completely transferring the second preparation (2) from Container (C2) to Container (C1)—which already contains the first preparation (1). In this case, the size of Container (C1) should be selected such that Container (C1) can receive the total quantity of the preparations (1) and (2) and also allows the two preparations (1) and (2) to be mixed by shaking or stirring, for example.

Another possibility of producing the application mixture is to completely transfer both preparations (1) and (2) from Containers (C1) and (C2) to a third container, which then allows the two agents to be mixed by shaking or stirring, for example.

The kit-of-parts can also comprise a third, separately packaged preparation (3). This is the case particularly if the preparation (1), which contains the compound I of the Formula (I) and, where applicable, compound II of the Formula (II), are to be packaged in an anhydrous manner.

In this case, the preparation (1) containing compound I of the Formula (I) and, where applicable, the compound II of the Formula (II) is first mixed with the aqueous preparation (3) - this mixing process guarantees to completely dissolve the compounds I of Formula (I) and also, where applicable, compounds II of Formula (II). To produce the final application mixture, the mixture of the preparations (1) and (3) is then mixed with the preparation (2), thereby setting the optimal pH value for application.

In this case, a particularly preferred kit-of-parts is therefore exemplified in that the first preparation (1) has a water content from about 0 to about 5.0 wt. %, preferably from about 0 to about 2.5 wt. %, more preferably from about 0 to about 1.0 wt. %, most preferably from about 0 to about 0.1 wt. %, relative to the total weight of the first preparation (1).

the kit-of-parts comprises at least one other preparation, which is packaged separately from preparations (1) and (2), wherein the third preparation (3)—relative to the total weight of the preparation (3)—has a water content of from about 5.0 to about 99.0 wt. %, more particularly from about 15.0 to about 85.0 wt. %.

The preparations (1), (2), as well as (3) where applicable, can also contain additional active ingredients, adjuvants and additives in order to improve the decoloration effect and set further desired properties of the agent. Examples are one or more preparations of additional non-ionic polymers, such as vinylpyrrolidinon/vinylacrylat-copolymers, polyvinylpyrrolidinon, vinylpyrrolidinon/vinylacetat-copolymers, poly ethylengly cols and polysiloxanes; additional silicones such as volatile or non-volatile, straight-chained, branched or cyclical, cross-linked or non-cross-linked polyalkylsiloxanes (such as dimethicones or cyclomethicones), polyarylsiloxanes and/or polyalkylarylsiloxanes, more particularly polysiloxanes with organofunctional groups such as subtituted or unsubstituted amines (amodimethicones), carboxyl-, alkoxy- and/or hydroxyl groups (dimethiconcopolyols), lineare polysiloxan(A)-polyoxyalkylen(B)-block copolymers, grafted silicon polymers; cationic polymers such as quaternized cellulose ether, polysiloxanes with quaternary groups, dimethyldiallylammoniumchlorid-polymers, acrylamid-dimethyldiallyl-ammonium chloride copolymers, with diethylsulfate quaternated dimethylaminoethylmethacrylat-vinylpyrrolidinon-copolymers, vinylpyrrolidinon-imidazolinium-methochlorid-copolymers and quaternated polyvinylalcohol; zwitterionic and amphoteric polymers; anionic polymers such as polyacryl acids or cross-linked polyacryl acids; structurants, such as glucose, malic acid and lactic acid, hair-conditioning compounds such as phospholipides, for example lecithin and kephaline; perfume oils, dimethylisosorbid and cyclodextrine; fiber structure-improving agents, more particularly mono-, di- and oligosaccharides, such as glucose, galactose, fructose, fruit sugar and lactose; dyes for coloring the preparations; anti-dandruff active ingredients such as piroctone olamine, zinc omadine and climbazol; amino acids and oligopeptides; protein hydrolysates on an animal and/or plant basis, as well as in the form of their fatty acid condensation products or, where applicable, anionically or cationically modified derivatives; plant oils; light stabilizers and UV blockers; active ingredients such as panthenol, pantothenic acid, pantolacton, allantoin, pyrrolidinoncarbonic acids and the salts thereof, as well as bisabolol; polyphenols, more particularlyhydroxy cinnamic acids, 6,7-dihydroxycumarines, hydroxybenzoic acids, catechins, tannins, flavanons, anthocyanidines, flavanons, flavons and flavonols; ceramides or pseudoceramides; vitamins, provitamins and vitamin precursors; plant extracts; fats and waxes such as fatty alcohols, beeswax, montan wax and parafins; source and pentration substances such as glycerin, propylenglycolmonoethylether, carbonate, hydrogen carbonate, guanidine, urea, as well as primary, secondary and tertiary phosphates; opacifiers such as latex, styrene/PVP and styrene/acrylamide copolymers; pearl shine concentrates such as ethylenglycolmono- and— distearate as well as PEG-3-distearate; pigments as well as propellants such as propane-butane-mixtures, $N_2O$, dimethylether, $CO_2$ and air. In this context, explicit reference is made to the known monographies, e.g. Kh. Schrader, Grundlagen und Rezepturen der Kosmetika [Cosmetic principles and formulas, 2nd Edition, Hiithig Buch Verlag, Heidelberg, 1989, which reflect the corresponding knowledge of a person skilled in the art With respect to the more preferred embodiments of the kit-of-parts as contemplated herein, the agents mentioned in the present disclosure apply mutatis mutandis.

The agents and kits-of-parts as contemplated herein described above can be used in processes to color and reductively decolor keratinous fibers, more particularly human hair.

A third subject matter of the present disclosure is therefore a method for coloring and reductively decoloring keratinous fibers, more particularly human hair, comprising the following process steps in the stated sequence a) Application of a cosmetic colorant containing at least one partially oxidizing dye and/or at least one oxidative dye precursor to keratinous fibers
b) Allowing the colorant to take effect for a period of from about 5 to about 60 minutes
c) Rinsing out the colorant
d) Application of a cosmetic agent or a decoloration agents as contemplated herein produced from the kit-of-parts as contemplated herein to keratinous fibers,
e) Allowing the colorant to take effect at from about 15 to about 45° C. for a period of from about 5 to about 60 minutes, preferably from about 10 to about 55 minutes, more preferably from about 15 to about 55 minutes, most preferably from about 20 to about 50 minutes,
f) Rinsing out the decoloration,
g) Where necessary, application of a post-treatment agent to the keratinous fibers, wherein said post-treatment agent contains at least one tenside from the group of anionic tensides, cationic tensides, non-ionic tensides, amphoteric and/or zwitterionic tensides, as well as the mixtures thereof.

The method for coloring and reductively decoloring keratinous fibers as contemplated herein improves the decoloration process and reduces the unpleasant odor compared to methods known from the prior art.

Steps a), b) and c) of the method constitute the coloration process of the keratinous fibers and are therefore executed in a direct temporal sequence in succession. In principle, there is no time limitation for the sequence of steps c) and d). For example, step d) can take place hours, days or even six weeks after step c) is complete.

However, the method is intended to remove the unwanted color result of the coloring process in steps a) to c). Therefore, it is obvious that the decoloration can take place only when the colored fibers show the unwanted color result. If the keratin fibers were colored with partially oxidizing dyes, for example, and this color has completely washed out after about 2 weeks, a subsequent decoloration process is neither necessary nor addressed by the present disclosure.

In step d) of the method as contemplated herein, a cosmetic agent of the first subject matter of the present disclosure or an agent produced from the kit-of-parts as contemplated herein is applied to the keratinous fibers.

Steps d), e) and f) of the method constitute the decoloration process of the keratinous fibers and are therefore executed in a direct temporal sequence in succession.

Step g) of the method, i.e. application of a post-treatment agent, is optional. Likewise, there is no time limitation for the sequence of step f) and the optional step g). It is, however, advantageous for step g) to take place within two days of step f) being completed. The post-treatment step g) can also be repeated more than once, if the post-treatment agent is a shampoo, for example.

The coloration preparation and the decoloration preparation as contemplated herein are normally applied by hand by the user. Personal protective clothing is preferably worn in the process, more particularly protective gloves, preferably from plastic or latest for one-time use (disposable gloves), as well as an apron. However, the coloration agent and decoloration preparation can also be applied to the keratin fibers by employing an application aid.

With respect to the cosmetic agent as contemplated herein, the agent produced from the kit of parts as contemplated herein, as well as other preferred embodiments of the method as contemplated herein, the statements made about the cosmetic means and the kit-of-parts as contemplated herein apply mutatis mutandis.

Moreover, a further subject matter of the present disclosure is the use of a cosmetic agent as contemplated herein or of a cosmetic agent produced from the kit of parts as contemplated herein for decoloring colored keratinous fibers, more particularly human hair. The use of said agents improves the decoloration of dyed keratinous agents and prevents post-darkening or re-coloration. Moreover, the unpleasant odor produced during the decoloration process is reduced compared to agents known from the prior art.

Finally, a further subject matter of the present disclosure is the use of a cosmetic agent as contemplated herein or of a cosmetic agent produced from the kit of parts as contemplated herein for reducing the unpleasant odor produced during the decoloration of dyed keratinous fibers.

With respect to the preferred embodiments of the use as contemplated herein, the statements made about the cosmetic agent as contemplated herein apply mutatis mutandis.

In summary, the present disclosure is outlined in particular by the following items:

1. Cosmetic agent for the reductive decoloration of dyed keratinous fibers, more particularly human hair, containing in a cosmetic carrier
a) at least compound of I of the Formula (I)

wherein
   A denotes $N(R^3)_{3-q}$ or $O(R^4)_{2-p}$
   $R^1$, $R^2$, $R^4$ denote independently a hydrogen atom or a $C_1$-$C_6$-alkyl group,
   $R^3$ denotes identical or various radicals selected from a hydrogen atom, a $C_1$-$C_{20}$ alkyl group, a $C_3$-$C_8$ cycloalkyl group, substituted by one to three $C_1$-$C_4$ alkyl radicals if necessary
   M denotes identical or various residues selected from a hydrogen atom or an equivalent of an alkali, alkali earth or metal ions, more particularly for sodium, potassium, ½ magnesium, ½ calcium, ½ zinc, or an ammonium ion ($NH_4^+$),
   p denotes the integer 1 or 2,
   q denotes the integer 2 or 3,
   wherein
   at least one of the radicals $R^1$, $R^2$, $R^4$ denotes a $C_1$-$C_6$ alkyl group, if A denotes $O(R^4_{2-p})$, and
   $R^3$ does not denote a hydrogen atom if q is equal to about 1, and
b) at least one alcohol with from about 10 to about 30 hydrogen atoms in a total quantity of from about 0.1 to about 20 wt. %, relative to the total weight of the cosmetic agent.

2. Cosmetic agent according to Item 1, exemplified in that it contains at least one compound I of the Formula (Ia)

3. Cosmetic agent according to one of the items 1 or 2, exemplified in that the cosmetic agent contains the at least one compound I of the Formula (I) in a total quantity of from about 0.1 to about 30.0 wt. %, preferably from about 0.2 to about 20.0 wt. %, more preferably from about 0.3 to about 10.0 wt. %, and most preferably from about 0.5 to about 6.0 wt. %, relative to the total weight of the cosmetic agent.

4. Cosmetic agent according to one of the aforementioned items, exemplified in that the at least one alcohol b) has from about 10 to about 30 carbon atoms selected from the group of 1-decanol, lauryl alcohol, myristyl alcohol, cetyl alcohol, stearyl alcohol, arachylalcohol and behenyl alcohol, lignoceryl alcohol, ceryl alcohol, montanyl alcohol, as well as the mixtures thereof, more particularly from a mixture of cetyl alcohol and stearyl alcohol 5. Cosmetic agent according to one of the aforementioned items, exemplified in that the at least one alcohol is contained in a total quantity of from about 0.5 to about 18 wt. %, preferably from about 1.0 to about 15 wt. %, more preferably from about 1.2 to about 12 wt. %, and most preferably from about 1.5 to about 10 wt. %, relative to the total weight of the cosmetic agent.

6. Cosmetic agent according to one of the aforementioned items, exemplified in that it contains in addition a compound II of the Formula (II)

wherein
   A denotes $N(R^3)_{3-q}$ or $O(R^4)_{2-p}$
   $R^1$, $R^2$, $R^4$ denote independently a hydrogen atom or a $C_1$-$C_6$-alkyl group,
   $R^3$ denotes identical or various radicals selected from a hydrogen atom, a $C_1$-$C_{20}$ alkyl group, a $C_3$-$C_8$ cycloalkyl group, substituted by one to three $C_1$-$C_4$ alkyl radicals if necessary
   M denotes identical or various residues selected from a hydrogen atom or an equivalent of an alkali, alkali earth or metal ions, more particularly for sodium, potassium, ½ magnesium, ½ calcium, ½ zinc, or an ammonium ion ($NH_4^+$),
   p denotes the integer 1 or 2,
   q denotes the integer 2 or 3,
   wherein
   at least one of the radicals $R^1$, $R^2$, $R^4$ denotes a $C_1$-$C_6$ alkyl group, if A denotes $O(R^4_{2-p})$, and
   R3 does not denote a hydrogen atom if q is equal to 1, 7. Cosmetic agent according to Item 6, exemplified in that it contains at least one compound II of the Formula (IIa)

8. Cosmetic agent according to one of the items 6 or 7, exemplified in that the at least one compound II of the Formula (II) is contained in a total quantity of from about 0.1 to about 30.0 wt. %, preferably from about 0.2 to about 20.0 wt. %, more preferably from about 0.3 to about 10.0 wt. %, and most preferably from about 0.5 to about 6.0 wt. %, relative to the total weight of the cosmetic agent.

9. Cosmetic agent according to one of the aforementioned items, exemplified in that it exists in the form of an emulsion.

10. Kit-of-parts for the reductive decoloration of dyed keratinous fibers, comprising at least two preparations (1) and (2) packaged separately from one another, wherein the first preparation (1) in a cosmetic carrier contains at least one compound I of the Formula (I), and where applicable at least one compound II of the Formula (II), as defined in the first subject matter of the present disclosure, and the second preparation (2) contains at least one inorganic and/or organic acid, wherein preparation (1) and/or preparation (2) contains at least one alcohol with from 10 to about 30 carbon atoms in a total quantity of from about 0.1 to about 20 wt. %, relative to the total weight of preparation (2).

11. Kit-of-parts according to Item 10, exemplified in that the second preparation (2) contains at least one organic acid, selected from the group of citric acid, tartaric acid, malic acid, lactic acid, acetic acid, sulphuric acid, hydrochloric acid, phosphoric acid, methane sulfonic acid, benzoic acid, malonic acid, oxalic acid, pyruvic acid, oxalocetic acid (oxobutanic acid), oxal acetic acid ester, 1-hydroxyethane-1,1-diphosphonic acid, as well as the mixtures thereof.

12. Kit-of-parts according to one of the Items 10 and 11, exemplified in that the second preparation (2) exists in the form of an emulsion.

13. Method for coloration and reductive coloration of keratinous fibers, more particularly human hair, comprising the following method steps in the stated sequence (a) Application of a cosmetic colorant containing at least one partially oxidizing dye and/or at least one oxidative dye precursor to keratinous fibers (b) Allowing the colorant to take effect for a period of from about 5 to about 60 minutes (c) Rinsing out the colorant (d) Application of a decoloration agent according to one of the Items 1 to 9 or of a decoloration agent produced from a kit-of-parts according to one of the Items 10 to 12 onto keratinous fibers, (e) Allowing the colorant to take effect at from about 20 to about 45° C. for a period of from about 5 to about 60 minutes, preferably from about 10 to about 55 minutes, more preferably from about 15 to about 55 minutes, most preferably from about 20 to about 50 minutes, (f) Rinsing out the decoloration agent, (g) Where necessary, application of a post-treatment agent to the keratinous fibers, wherein said post-treatment agent contains at least one tenside from the group of anionic tensides, cationic tensides, non-ionic tensides, amphoteric and/or zwitterionic tensides, as well as the mixtures thereof.

14. Use of a cosmetic agent according to one of the Items 1 to 9 or a cosmetic agent produced from a kit-of-parts according to one of the Items 10 to 12 for decoloring dyed keratinous fibers, more particularly human hair.

15. Use of a cosmetic agent according to one of the Items 1 to 9 or a cosmetic agent produced from a kit-of-parts according to one of the Items 10 to 12 for reducing the unpleasant odor produced during the decoloration dyed keratin fibers.

The examples below explain, but do not limit preferred embodiments.

EXAMPLES

1.1. Coloration

The following formulations were produced (all data in wt. %):

Dye Cream (F1)

| Raw material | wt. % |
| --- | --- |
| Cetearyl alcohol | 6.6 |
| C12-C18 fatty alcohols | 2.4 |
| Ceteareth-20 | 0.6 |
| Ceteareth-12 | 0.6 |
| Plantacare 1200 UP (laurylglucoside, 50-53% hydrous solution) | 2.0 |
| Sodium laureth-6 carboxylate (21% i hydrous solution) | 10.0 |
| Sodium myreth sulfate (68-73% hydrous solution) | 2.8 |
| Sodium acrylate, trimethylammoniopropylacrylamide chloride copolymer (19-21% hydrous solution) | 3.8 |
| Sodium hydroxide | 0.26 |
| p-toluylendiamine, sulfate | 0.48 |
| m-aminophenol | 0.02 |
| 4-chlorresorcin | 0.09 |
| 2-Methyl resorcin | 0.04 |
| Resorcin | 0.12 |
| Ammonium sulfate | 0.71 |
| Sodium sulfate | 0.4 |
| Ascorbic acid | 0.1 |
| 1-Hydroxyethane-1,1-diphosphonic acid (60% hydrous solution) | 0.2 |
| Sodium soluble glass | 0.5 |
| L-Serin | 1.0 |
| Ammonia (25% hydrous solution) | 6.7 |
| Water | ad 100 |

Dye Cream (F2)

| Raw material | wt. % |
| --- | --- |
| Cetearyl alcohol | 8.5 |
| C12-C18 fatty alcohols | 2.4 |
| Ceteareth-20 | 0.6 |
| Ceteareth-12 | 0.6 |
| Plantacare 1200 UP (laurylglucoside, 50-53% hydrous solution) | 2.0 |
| Sodium laureth-6 carboxylate (21% i hydrous solution) | 10.0 |
| Sodium myreth sulfate (68-73% hydrous solution) | 2.8 |
| Sodium acrylate, trimethylammoniopropylacrylamide chloride copolymer (19-21% hydrous solution) | 3.8 |
| Potassium hydroxide | 0.83 |
| p-toluylendiamine, sulfate | 0.89 |
| m-Aminophenol | 0.04 |
| 2-Methyl resorcin | 0.10 |
| Resorcin | 0.17 |
| 4-chlorresorcin | 0.08 |
| 2-amino-3-methylphenol | 0.03 |
| 2,7-dihydroxynaphthalin | 0.09 |
| Glycin | 1.0 |
| Sodium sulfate | 0.4 |
| Ascorbic acid | 0.1 |
| 1-Hydroxyethane-1,1-diphosphonic acid (60% hydrous solution) | 0.2 |
| Sodium soluble glass | 0.5 |
| Marula oil | 0.6 |
| Monoethanolamine | 5.0 |
| Water | Ad 100 |

Oxidant (Ox)

| Raw material | wt. % |
| --- | --- |
| Sodium benzoate | 0.04 |
| Dipicolinic acid | 0.1 |
| Di-sodium pyrophosphate | 0.1 |
| Potassium hydroxide | 0.09 |
| 1,2-Propylenglycol | 1.0 |
| 1-Hydroxyethane-1,1-diphosphonic acid (60% hydrous solution) | 0.25 |
| Paraffinum Liquidum | 0.30 |

| Raw material | wt. % |
| --- | --- |
| Steartrimonium chloride | 0.39 |
| Cetearyl alcohol | 3.4 |
| Ceteareth-20 | 1.0 |
| Hydrogen peroxide (50% hydrous solution) | 12.0 |

Hair strands (Kerling Euro natural hair, white) were measured by colorimetry, the L-value (as a degree of lightness of the hair strands) was determined in each case.

The dye creams (F1 and F2) and the oxidant (Ox) were then mixed together in a ratio of 1:1 and applied to the hair strands (Kerling Euro natural hair, white). The weight ratio of the application mixture: Hair 4:1, exposure time 30 minutes at a temperature of 32 degrees Celsius. The strands were then rinsed with water, dried and left to rest at room temperature for at least 24 hours.

The hair strands were then measured by colorimetry, the L-value (as a degree of lightness of the hair strands) was again determined.

The strands were colored a dark blond shade (F1+OX) and/or a mocha brown shade (F2+Ox).

1.2 Decoloration

The following decoloration agents were produced (all data in wt. %)

Preparations (1) with pH Value from 6.0-10.5

| Raw material | Z1-1 | Z1-2 | Z1-3 | Z1-4 |
| --- | --- | --- | --- | --- |
| Xanthan Gum | 0.8 | 0.8 | 0.6 | 0.6 |
| Propylene gylcol | 1.6 | 1.6 | 1.2 | 1.2 |
| Cocamidopropylbetain (40%) | 4.0 | 4.0 | 3.0 | 3.0 |
| Cyclanon Eco (hydrous solution of the compound of Formula (Ia) and (IIa) in the molar ratio 1:1) | 20 | — | — | 40 |
| Sodium dithionit | — | 20 | 40 | — |
| Water | Ad 100 | Ad 100 | Ad 100 | Ad 100 |

Preparations (2) with pH Value from 0.5-2.0

| Raw material | Z2-1 (gel) | Z2-2 (emulsion) |
| --- | --- | --- |
| Xanthan Gum | 0.9 | — |
| Propylene gylcol | 1.8 | — |
| Cocamidopropylbetain (40%) | 4.4 | — |
| Sulphuric acid (20%) | 12 | 5.3 |
| Oxalic acid | — | 0.67 |
| Emulgade FT [1)] | — | 2.8 |
| Water | Ad 100 | Ad 100 |

[1)] 77 wt. % cetearyl alcohol, 15 wt.-% PEG-40 Castor Oil, 7.5 wt. % sodium cetearyl sulfate (INCI: CETEARYL ALCOHOL, PEG-40 CASTOR OIL, SODIUM CETEARYL SULFATE; BASF)

Preparations (3)

| Raw material | Z3-1 | Z3-2 |
| --- | --- | --- |
| Xanthan Gum | 0.9 | 0.9 |
| Propylene gylcol | 1.8 | 1.8 |
| Cocamidopropylbetain (40%) | 4.5 | 4.5 |
| Cyclanon Eco (hydrous solution of the compound of Formula (Ia) and (IIa) in the molar ratio 1:1) | 10 | — |
| Sodium dithionit | — | 10 |
| Sulphuric acid, 20% | Ad pH 1.8 | Ad pH 1.8 |
| Water | Ad 100 | Ad 100 |

To produce each of the ready-to-use decoloration agents, preparations Z1-1 to Z1-4 were mixed with one of the preparations Z2-1 or Z2-2. Preparations Z3-1 and Z3-2 were used as a decoloration agent immediately after production. All decoloration agents have a pH value of from about 1.5 to about 3.5.

| decoloration agent | Produced from |
| --- | --- |
| 1 | Z1-1 + Z2-1 in the ratio 1:1 |
| 2 | Z1-2 + Z2-1 in the ratio 1:1 |
| 3 | Z1-3 + Z2-2 in the ratio 1:3 |
| 4* | Z1-4 + Z2-2 in the ratio 1:3 |
| 5 | Z3-1 |
| 6 | Z3-2 |

*Example according to the present disclosure

Decoloration agent 4 as contemplated herein was applied to the hair, wherein the mixture ratio of application mixture: hair was 4:1. After an exposure time of 30 minutes at a temperature of 32 degrees Celsius, the strands were rinsed with water, dried and left to rest at room temperature for at least 24 hours.

The hair strands were then measured by colorimetry, the L-value (as a degree of lightness of the hair strands) was again determined.

The decoloration result was assessed by determining the $\Delta L$ value $\Delta L = L$ (after decoloration)$-L$ (before coloration)

The higher the $\Delta L$ value, the more effectively the dyed hair strands were decolored.

| | L-value | ΔL-value |
| --- | --- | --- |
| F1 + OX | | |
| Colored hair | 33.1 | 23.8 |
| Decolored hair | 56.9 | |
| F2 + OX | | |
| Colored hair | 25.7 | 25.5 |
| Decolored hair | 51.2 | |

Both the strands colored with F1+OX and also the strands colored with F2+OX were significantly decolored after application of the decoloration agent 4 as contemplated herein.

Moreover, the unpleasant odor during decoloration was determined. This was done using 4 g of the decoloration agent concerned per 1 g of oxidatively colored hair strands. After 5 minutes at 32° C, the unpleasant odor during decoloration was determined and evaluated by employing a rating system (1=very slight unpleasant odor, 2=slight unpleasant odor, 3=medium unpleasant odor, 4=strong unpleasant odor). The results are shown in the table below:

| Decoloration agent | Unpleasant odor |
| --- | --- |
| 1 | 2 |
| 2 | 4 |

| Decoloration agent | Unpleasant odor |
|---|---|
| 3 | 3 |
| 4* | 1 |
| 5 | 3 |
| 6 | 4 |

*Example according to the present disclosure

The use of an emulsion containing an alcohol with from 10 to 30 carbon atoms in combination with reducing agents of the Formulas (Ia) and (IIa) was able to substantially reduce the unpleasant odor during the decoloration process.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A cosmetic agent for the reductive decoloration of dyed hair, comprising:
    a preparation (1) and a preparation (2), wherein the preparation (1) consists of xanthan gum, propylene glycol, cocamidopropyl betaine, a compound of formula (I) wherein the compound of formula (I) is $N(CH_2SO_2Na)_3$, a compound of formula (II) wherein the compound of formula (II) is $N(CH_2SO_3Na)_3$, and water; and
    wherein the preparation (2) consists of sulfuric acid, oxalic acid, cetearyl alcohol, PEG-40 Castor Oil, sodium cetearyl sulfate, and water.

2. A method for reductive decoloration of dyed hair, comprising:
    (a) applying the cosmetic agent of claim 1 to the dyed hair.

* * * * *